(12) United States Patent
Lee et al.

(10) Patent No.: US 9,987,162 B2
(45) Date of Patent: Jun. 5, 2018

(54) MAMMALIAN HEAD COOLING SYSTEM AND METHOD

(71) Applicant: The University of Western Ontario, London, Ontario (CA)

(72) Inventors: Ting-Yim Lee, London (CA); Mohammad Fazel Bakhsheshi, London (CA); Lynn Keenliside, Lucan (CA)

(73) Assignee: THE UNIVERSITY OF WESTERN ONTARIO, Ontario (CA)

( * ) Notice: Subject to any disclaimer, the term of this patent is extended or adjusted under 35 U.S.C. 154(b) by 0 days. days.

(21) Appl. No.: 15/127,737

(22) PCT Filed: Mar. 20, 2015

(86) PCT No.: PCT/CA2015/050216
§ 371 (c)(1),
(2) Date: Sep. 20, 2016

(87) PCT Pub. No.: WO2015/139142
PCT Pub. Date: Sep. 24, 2015

(65) Prior Publication Data
US 2017/0143538 A1 May 25, 2017

Related U.S. Application Data

(60) Provisional application No. 61/968,844, filed on Mar. 21, 2014.

(51) Int. Cl.
*A61F 7/12* (2006.01)
*A61M 16/06* (2006.01)
(Continued)

(52) U.S. Cl.
CPC ........... *A61F 7/12* (2013.01); *A61M 16/0666* (2013.01); *A61M 16/0875* (2013.01);
(Continued)

(58) Field of Classification Search
CPC .. A61M 16/00; A61M 16/0875; A61M 16/10; A61M 16/1075; A61M 16/1095;
(Continued)

(56) References Cited

U.S. PATENT DOCUMENTS 1,952,281 A 3/1934 Ranque
3,291,126 A * 12/1966 Messick ............. A41D 13/0053
128/201.29
(Continued)

FOREIGN PATENT DOCUMENTS

CN 201248938 Y 6/2009
WO WO 2010/148372 A1 12/2010
(Continued)

OTHER PUBLICATIONS

Andrews PJ et al (2011) "European society of intensive care medicine study of therapeutic hypothermia (32-35° C.) for intracranial pressure reduction after traumatic brain injury (the Eurotherm3235Trial)" *Trials* 12:8 (in 13 pages).
(Continued)

*Primary Examiner* — Tan-Uyen (Jackie) T Ho
*Assistant Examiner* — Joseph D Boecker
(74) *Attorney, Agent, or Firm* — Knobbe, Martens, Olson & Bear, LLP

(57) ABSTRACT

Described herein is a head cooling system comprising: a source of compressed breathable gas; a vortex tube comprising an inlet, a hot gas outlet and a cold gas outlet, the inlet operably connected to the source of compressed breathable gas; and an interface for delivering cooled gas to a nasopharyngeal cavity in fluid communication with the cold gas outlet. The head cooling system may be used in a method to reduce neurodegeneration in a subject, for example neurodegeneration from ischemia, anoxia, cardiac arrest, trauma or neurodegenerative disease. The head cooling system may also be used in a method to prophylactically protect a subject
(Continued)

at risk of neurodegeneration, for example neurodegeneration from ischemia, anoxia, cardiac arrest, trauma or neurodegenerative disease.

22 Claims, 21 Drawing Sheets

(51) Int. Cl.
*A61M 16/08* (2006.01)
*A61M 16/20* (2006.01)
*A61F 7/00* (2006.01)

(52) U.S. Cl.
CPC ... *A61M 16/202* (2014.02); *A61F 2007/0006* (2013.01); *A61F 2007/0064* (2013.01); *A61F 2007/0096* (2013.01); *A61M 2205/3331* (2013.01); *A61M 2205/3368* (2013.01); *A61M 2205/3606* (2013.01); *A61M 2206/16* (2013.01)

(58) Field of Classification Search
CPC .. A61M 2021/0066; A61M 2205/3606; A61M 2206/16; A61F 7/12; A61F 2007/0006; A61F 2007/0064
USPC ............ 128/200.24, 201.13, 201.23, 201.28, 128/201.29, 202.19, 204.15, 204.17, 128/204.25, 205.24, 897
See application file for complete search history.

(56) References Cited

U.S. PATENT DOCUMENTS

| | | | | |
|---|---|---|---|---|
| 3,815,573 A * | 6/1974 | Marcus | ................... | B63C 11/28 126/204 |
| 3,898,978 A * | 8/1975 | Marcus | ................... | B63C 11/28 126/204 |
| 4,240,261 A | 12/1980 | Inglis | | |
| 5,261,399 A | 11/1993 | Klatz et al. | | |
| 5,386,823 A * | 2/1995 | Chen | ................... | A41D 13/0053 128/201.24 |
| 5,913,885 A | 6/1999 | Klatz et al. | | |
| 5,916,242 A | 6/1999 | Schwartz | | |
| 6,228,106 B1 * | 5/2001 | Simbruner | ............. | A41B 13/00 2/69 |
| 6,312,453 B1 | 11/2001 | Stefanile et al. | | |
| 6,682,552 B2 | 1/2004 | Ramsden et al. | | |
| 8,308,786 B2 | 11/2012 | Rozenberg et al. | | |
| 8,512,280 B2 | 8/2013 | Rozenberg et al. | | |
| 2002/0129818 A1 * | 9/2002 | Morgan | ................. | A62B 18/08 128/206.26 |
| 2006/0112698 A1 | 6/2006 | Cazzini et al. | | |
| 2006/0212103 A1 * | 9/2006 | Wagner, III | ............. | A61F 7/02 607/108 |
| 2006/0276552 A1 | 12/2006 | Barbut et al. | | |
| 2008/0015543 A1 | 1/2008 | Wang | | |
| 2012/0031405 A1 * | 2/2012 | Geist | ..................... | A61F 7/0085 128/204.15 |
| 2013/0331915 A1 | 12/2013 | Rozenberg et al. | | |
| 2014/0260335 A1 * | 9/2014 | Beeler | ....................... | F25B 9/04 62/5 |
| 2016/0228669 A1 * | 8/2016 | Hadash | ................. | A61M 16/06 |

FOREIGN PATENT DOCUMENTS

WO WO 2011/156409 A1 12/2011
WO WO 2015/040614 A1 3/2015

OTHER PUBLICATIONS

Azzopardi, D. et al. 2009 "Treatment of asphyxiated newborns with moderate hypothermia in routine clinical practice: how cooling is managed in the UK outside a clinical trial" *Arch Dis Child Fetal Neonatal Ed* 94:F260-F264.
Bakhsheshi MF. Nasopharyngeal method for selective brain cooling and development of a time-resolved near-infrared technique to monitor brain temperature and oxidation status during hypothermia. In: PhD Thesis, Department Medical Biophysics, Western University: LondonWestern University, (2014).
Bakhsheshi MF et al. 2016 "Efficacy of Selective Brain Cooling Using a Nasopharyngeal Method in Piglets" *Neurocrit Care* 24: 140-149.
Bakhsheshi MF et al. (2016) Control of rewarming rate following rapid selective brain cooling. 14th Annual Meeting of the Imaging Network Ontario (ImNO).
Bakhsheshi MF et al. (2016) "Rapid and selective brain cooling method using vortex tube: a feasibility study" *Am J Emerg Med* 34:887-894.
Bernard SA et al. (2002) "Treatment of comatose survivors of out-of-hospital cardiac arrest with induced hypothermia."*N Engl J Med* 346:557-563.
Boller M et al. (2010) "Feasibility of intra-arrest hypothermia induction: a novel nasopharyngeal approach achieves preferential brain cooling." *Resuscitation* 81:1025-1030.
Busch HJ et al (2010) "Safety and feasibility of nasopharyngeal evaporative cooling in the emergency department setting in survivors of cardiac arrest." *Resuscitation* 81:943-949.
Cabanac M (1993) Selective brain cooling in humans: "fancy" or fact? *FASEB J* 7:1143-1147.
Caputa M et al. 1991 "Selective brain cooling in rats resting in heat and during exercise." *J Therm Biol* 16: 19-24.
Caputa M et al. 1996 "Anatomical and physiological evidence for efficacious selective brain cooling in rats" *J Therm Biol* 21: 21-28.
Castrén M et al (2010) "Intra-arrest transnasal evaporative cooling: a randomized, prehospital, multicenter study (PRINCE: Pre-ROSC IntraNasal Cooling Effectiveness)." *Circulation* 122:729-736.
Cenic A et al. (1999) "Dynamic CT measurement of cerebral blood flow: a validation study." *AJNR Am J Neuroradiol* 20:63-73.
Cross B. 1996 "The Biology and Medicine of Rabbits and Rodents" 4th ed. *The Canadian Veterinary Journal* 37: 759-760.
Culic S (2005) "Cold injury syndrome and neurodevelopmental changes in survivors." *Arch Med Res* 36: 532-538.
Dohi K et al. (2006) "Positive selective brain cooling method: a novel, simple, and selective nasopharyngeal brain cooling method." *Acta Neurochir Suppl* 96:409-412.
Dudgeon DL et al. 1980 Mild hypothermia: Its effect on cardiac output and regional perfusion in the neonatal piglet. J Pediatr Surg 15:805-810.
Ehrlich MP et al. (2002) "Effect of hypothermia on cerebral blood flow and metabolism in the pig." *Ann Thorac Surg* 73:191-197.
Eiamsa-Ard S and Promvonge P (2008) "Review of Ranque-Hilsch effects in vortex tubes." *Renew Sust Energ Rev* 12:1822-1842.
Erecinska M et al. (2003) "Effects of hypothermia on energy metabolism in Mammalian central nervous system." *J Cereb Blood Flow Metab* 23:513-530.
Fin'Ko V (1983) "Cooling and condensation of a gas in a vortex flow." *Sov Phys Tech Phys* 28:1089-1093.
Go As et al. (2013) "Heart disease and stroke statistics—2013 update: a report from the American Heart Association." *Circulation* 127:e6-e245.
Guidelines for the Management of Severe Traumatic Brain Injury. J Neurotrauma 24 Suppl 1:S1-106, 2007.
Hassani H and Meyer S. 2010 "Hypothermia for neuroprotection in adults after cardiopulmonary resuscitation." *Am Fam Physician* 82: 477-478.
Hilsch R (1947) "The use of the expansion of gases in a centrifugal field as a cooling process." *Rev Sci Instrum* 18:108-113.
Holzer 2002 Mild therapeutic hypothermia to improve the neurologic outcome after cardiac arrest *N Engl J Med* 346: 549-56.
Hutchison 2008 "Hyperthermia therapy after traumatic brain injury in children" *N Engl J Med* 358: 2447-2456.
Ingelstedt S and Ivstam B (1951) "Study in the humidifying capacity of the nose." *Acta Otolaryngol* 39:286-290.

(56) References Cited

OTHER PUBLICATIONS

Jessen C 2001 "Selective brain cooling in mammals and birds." *Jpn J Physiol* 51: 291-301.
Jia X et al. 2008 "Improving neurological outcomes post-cardiac arrest in a rat model: Immediate hypothermia and quantitative EEG monitoring." *Resuscitation* 76:431-442.
Kern KB (2012) "Optimal treatment of patients surviving out-of-hospital cardiac arrest." *JACC Cardiovasc Interv* 5:597-605.
Kersten JR et al. (1997) "Isoflurane mimics ischemic preconditioning via activation of K(ATP) channels: reduction of myocardial infarct size with an acute memory phase." *Anesthesiology* 87:361-370.
Koht A et al. (1983) "Serum potassium levels during prolonged hypothermia." *Intensive Care Med* 9:275-277.
Koskela Ho (2007) "Cold air-provoked respiratory symptoms: the mechanisms and management." *Int J Circumpolar Health* 66:91-100.
Krieger DW and Yenari MA. 2004 Therapeutic hypothermia for acute ischemic stroke: what do laboratory studies teach us? *Stroke* 35: 1482-1489.
Kuboyama K et al. (1993) "Delay in cooling negates the beneficial effect of mild resuscitative cerebral hypothermia after cardiac arrest in dogs: a prospective, randomized study." *Crit Care Med* 21:1348-1358.
Lampe JW and Becker LB. 2011 "State of the art in therapeutic hypothermia." *Annu Rev Med* 62: 79-93.
Laver S et al. (2004) "Mode of death after admission to an intensive care unit following cardiac arrest." *Intensive Care Med* 30:2126-2128.
Lim E (2015) "Review of the clinical evidence and controversies in therapeutic hypothermia for survivors of sudden cardiac death." *Proceedings of Singapore Healthcare* 24:42-53.
Mathur NB et al. 2005 "Evaluation of who classification of hypothermia in sick extramural neonates as predictor of fatality." *J Trop Pediatr* 51:341-345.
McConaghy FF et al. 1995 "Selective brain cooling in the horse during exercise and environmental heat stress." *J Appl Physiol* 79: 1849-1854.
Mehra R (2007) "Global public health problem of sudden cardiac death." *J Electrocardiol* 40:S118-S122.
Moore EM et al. 2011 "Therapeutic hypothermia: benefits, mechanisms and potential clinical applications in neurological, cardiac and kidney injury." *Injury* 42: 843-854.
Munday KA et al. (1958) "Plasma electrolyte changes in hypothermia." *Thorax* 13:334-342.
Nielsen N. et al. 2013 "Targeted temperature management at 33° C. versus 36° C. after cardiac arrest" *N Engl J Med* 369: 2197-2206.
Nielsen N et al. (2014) Targeted temperature management after cardiac arrest. *N Engl J Med* 370:1356-1361.
Peberdy MA et al (2010) "Part 9: post-cardiac arrest care: 2010 American Heart Association guidelines for cardiopulmonary resuscitation and emergency cardiovascular care." *Circulation* 122: S768-S786.
Polderman KH et al. 2001 "Hypophosphatemia and hypomagnesemia induced by cooling in patients with severe head injury." *J Neurosurg* 94: 697-705.
Polderman KH et al. 2003 "The importance of magnesium in critically ill patients: a role in mitigating neurological injury and in the prevention of vasospasms." *Intensive Care Med* 29: 1202-1203.
Polderman KH (2004) "Application of therapeutic hypothermia in the intensive care unit. Opportunities and pitfalls of a promising treatment modality—part 2: practical aspects and side effects." *Intensive Care Med* 30:757-769.
Polderman KH et al. 2008 "Hypothermia therapy after traumatic brain injury in children." *N Engl J Med* 359: 1178-1180.
Polderman KH and Herold I (2009) "Therapeutic hypothermia and controlled normothermia in the intensive care unit: practical considerations, side effects, and cooling methods." *Crit Care Med* 37:1101-1120.
Polderman KH (2009) "Mechanisms of action, physiological effects, and complications of hypothermia." *Crit Care Med* 37:S186-S202.
Povlishock JT and Wei EP (2009) "Posthypothermic rewarming considerations following traumatic brain injury." *J Neurotrauma* 26:333-340.
Powers WJ et al. (1985) "Cerebral blood flow and cerebral metabolic rate of oxygen requirements for cerebral function and viability in humans." *J Cereb Blood Flow Metab* 5:600-608.
Quinn MW and Munyard PF 2010 "Treatment of asphyxiated newborns with moderate hypothermia in routine clinical practice: How cooling is managed in the UK outside a clinical trial." *Arch Dis Child Fetal Neonatal Ed* 95:F152 (in 2 pages).
Robertshaw D (2004) "Temperature regulation and the thermal environment. In: Reece WO (ed) Dukes' physiology of domestic animals, 12th edn. Cornell University Press, Ithaca and London.
Robinson BJ et al. (1997) "Mechanisms whereby propofol mediates peripheral vasodilation in humans. Sympathoinhibition or direct vascular relaxation?" *Anesthesiology* 86:64-72.
Roy B. 2002 in *Fundamentals of classical and statistical thermodynamics*, Wiley, pp. 608 and 96-104.
Sakoh M and Gjedde A (2003) "Neuroprotection in hypothermia linked to redistribution of oxygen in brain." *Am J Physiol Heart Circ Physiol* 285:H17-H25.
Sarkar S and Barks JD. 2010 "Systemic complications and hypothermia." *Semin Fetal Neonatal Med* 15: 270-275.
Schubert A (1995) "Side effects of mild hypothermia." *J Neurosurg Anesthesiol* 7:139-147.
Singer M et al. 2005 "Reversal of life-threatening, drug-related potassium-channel syndrome by glibenclamide." *Lancet* 365: 1873-1875.
Soliman HM et al. 2003 "Development of ionized hypomagnesemia is associated with higher mortality rates." *Crit Care Med* 31: 1082-1087.
Szczesny G et al. 2004 "Long-term anaesthesia using inhalatory isoflurane in different strains of mice—the haemodynamic effects." *Lab Anim* 38: 64-69.
Thoresen M et al. (2009) "Cooling combined with immediate or delayed xenon inhalation provides equivalent long-term neuroprotection after neonatal hypoxia-ischemia." *J Cereb Blood Flow Metab* 29:707-714.
Tooley JR et al. (2005) "Significant head cooling can be achieved while maintaining normothermia in the newborn piglet." *Arch Dis Child Fetal Neonatal Ed* 90:F262-F266.
Uray T et al. 2010 "Surface cooling for rapid induction of mild hypothermia after cardiac arrest: Design determines efficacy." *Acad Emerg Med* 17:360-367.
Vortec Innovative Compressed Air Technologies 2013 "Cold air guns" (available on the World-Wide Web at: Vortec.Nl/our-products/cold-air-guns/).
Weihs W et al (2011) "The importance of surface area for the cooling efficacy of mild therapeutic hypothermia." *Resuscitation* 82:74-78.
Weis J et al. (2009) "Noninvasive monitoring of brain temperature during mild hypothermia." *Magn Reson Imaging* 27:923-932.
Weisser J et al. (2001) "Influence of mild hypothermia on myocardial contractility and circulatory function." *Basic Res Cardiol* 96:198-205.
Wong KC. 1983 "Physiology and pharmacology of hypothermia." *West J Med* 138: 227-232.
Zenker W and Kubik S (1996) "Brain cooling in humans—anatomical considerations." *Anat Embryol (Berl)* 193:1-13.
Zydlewski AW and Hasbargen JA (1998) "Hypothermia-induced hypokalemia." *Mil Med* 163:719-721.

\* cited by examiner

SCUBA Twin cylinder (100 cubic feet each)

Nasopharyngeal Cooling by Nasal Catheter

Nasopharyngeal Cooling by Face Mask

| | Baseline | Cooling | | | Rewarming |
|---|---|---|---|---|---|
| Temp (°C) | 38.5 | 34 (after 2 hours) | 34 (after 4 hours) | 34 (after 6 hours) | 37.5 |
| CBF (ml/100g/min) | 35 | 22 | 24 | 25 | 35 |

MAMMALIAN HEAD COOLING SYSTEM AND METHOD

BACKGROUND OF THE INVENTION

Field of the Invention

The present invention relates to cooling of structures within the skull of a mammal, and more particularly to cooling of brain tissue.

Description of the Related Art

Lowering the temperature of the brain is known to reduce the chances of brain tissue damage when oxygenated blood supply to the brain is diminished as may occur during ischemic or anoxic events for example during stroke, cardiac arrest, respiratory arrest, suffocation, drowning, strangulation, electrocution or any other head or body trauma that disrupts the flow of oxygenated blood to the brain.

Clinical investigators have reported that mild and moderate hypothermia can be neuroprotective to reduce brain injury and decrease death and disability for a variety of acute brain injuries following severe head trauma, cardiac arrest, stroke and neonatal asphyxia. The neuroprotective benefits of hypothermia have been linked to the time to initiate cooling after injury, depth of cooling and re-warming rate. Clinical studies indicate that the temperature range associated with better outcomes appears to be 32-35° C. and has to be achieved as quickly as possible. However, cooling the whole body below 34° C. can cause complications including shivering, sclerema, skin erythema, renal failure, coagulopathy, pulmonary hypertension, myocardial ischemia and others. Consequently, to limit the deleterious effects of whole body cooling, only mild hypothermia, in which the brain temperature is decreased to 34° C. has been applied, whereas it is known that additional neuroprotection can be achieved by cooling the brain further and quickly at the outset.

Selective cooling of the head, and more particularly the brain region may provide a neuroprotective benefit while avoiding the deleterious effects of whole body hypothermia. Functional solutions along this line have been proposed, for example, in U.S. Pat. No. 5,261,399 (issued 16 Nov. 1993), U.S. Pat. No. 5,913,885 (issued 22 Jun. 1999), U.S. Pat. No. 5,916,242 (issued 29 Jun. 1999), U.S. Pat. No. 6,312,453 (issued 6 Nov. 2001), U.S. Pat. No. 6,682,552 (issued 27 Jan. 2004), U.S. Pat. No. 8,308,786 (issued 13 Nov. 2012), U.S. Pat. No. 8,512,280 (issued 20 Aug. 2013) and US Patent Application Publication Nos. 20060112698 (published 1 Jun. 2006), 20060276552 (published 7 Dec. 2006), 20130331915 (12 Dec. 2013) and International Application Publication No. WO2010148372 (23 Dec. 2010). However, each of these solutions suffers from insufficient cooling, insufficient localization of cooling, use of a toxic coolant and/or deleterious effects on skin contact points.

Accordingly, there is a continuing need for alternative head cooling systems.

SUMMARY OF THE INVENTION

In an aspect there is provided a head cooling system comprising:

a source of compressed breathable gas;

a vortex tube comprising an inlet, a hot gas outlet and a cold gas outlet, the inlet operably connected to the source of compressed breathable gas; and an interface for delivering cooled gas to a nasopharyngeal cavity in fluid communication with the cold gas outlet.

In another aspect there is provided a head cooling kit comprising:

a vortex tube comprising an inlet, a hot gas outlet and a cold gas outlet;

an interface for delivering cooled gas to a nasopharyngeal cavity in fluid communication with the cold gas outlet; and instructions for operably connecting the inlet to a source of compressed breathable gas and securing the interface to a subject.

In yet another aspect there is provided a method of reducing neurodegeneration in a subject comprising administering cooled breathable gas from the head cooling system or kit to the nasopharyngeal cavity of the subject.

In still another aspect there is provided a method of prophylactically protecting a subject at risk of neurodegeneration comprising administering cooled breathable gas from the head cooling system or kit to the nasopharyngeal cavity of the subject.

In a further aspect there is provided a method for nasopharyngeal cooling, comprising:

supplying pressurized breathable gas from a source of compressed breathable gas;

receiving the pressurized breathable gas from the source of compressed breathable gas at a vortex tube and outputting cooled breathable gas from the vortex tube at a first temperature level in response to the pressurized breathable gas;

receiving the cooled breathable gas from the vortex tube through an interface and supplying a nasopharyngeal cavity with the cooled breathable gas.

DETAILED DESCRIPTION OF PREFERRED EMBODIMENTS

Figure 1:
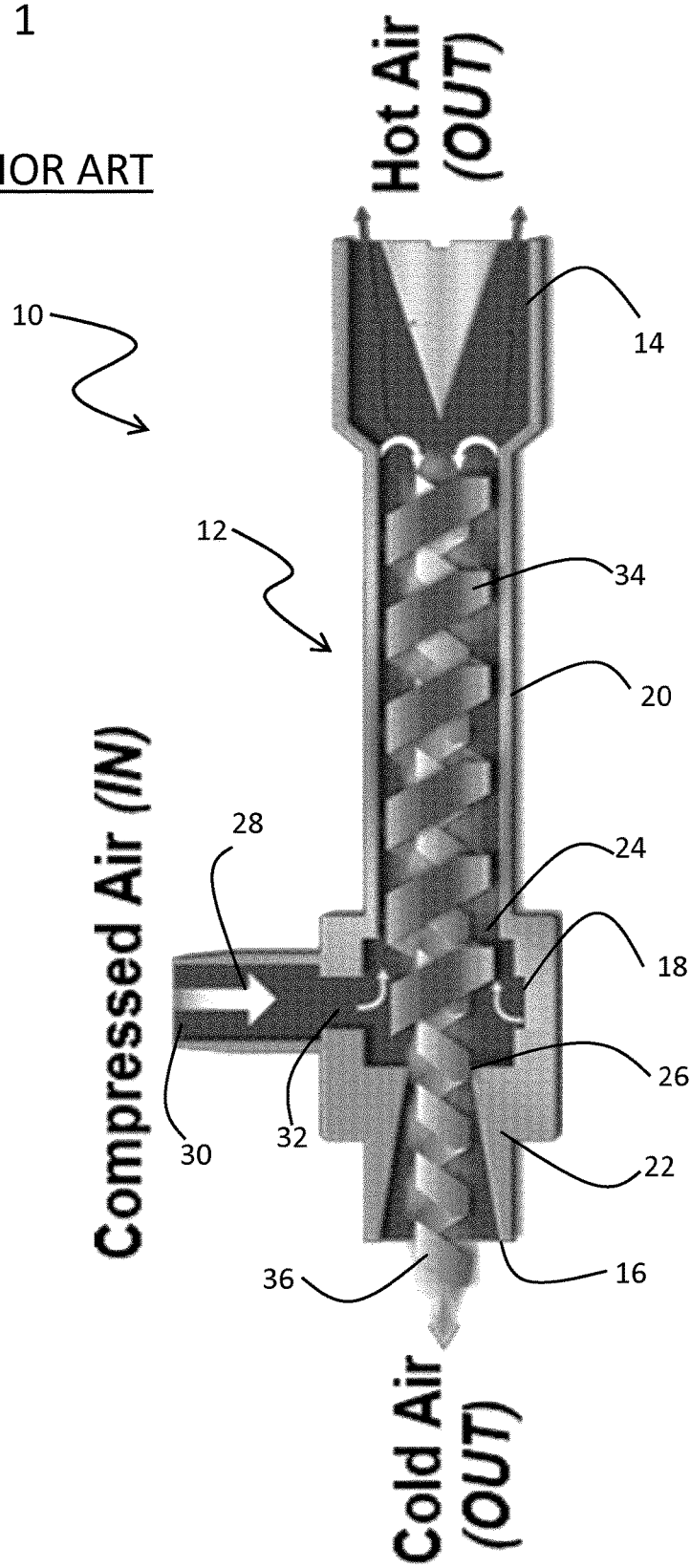
FIG. 1 shows an axial cross-section view of a vortex tube.

Now referring to the drawings, a head cooling system will be described. The head cooling system comprises a source of compressed breathable gas, a cooled gas generator, and an interface for delivering cooled gas through a nasal orifice, and optionally through an oral orifice of a subject. The head cooling system may be used therapeutically or prophylactically. The cooling system will typically be capable of achieving a brain temperature of less than about 34 degrees Celsius with a brain versus rectal temperature difference of greater than about 4 degrees Celsius.

The source of compressed breathable gas may be an electrical compressor or a tank or combinations thereof. Such sources are readily available in hospital and emergency first responder settings. A breathable gas includes oxygen generally at a partial pressure of oxygen of about 16 kiloPascals (0.16 bar) to 180 kiloPascals (1.80 bar) at ambient pressure. A breathable gas will typically have a volume fraction of oxygen of at least about 16%, more typically at least about 20%. Typically, the cheapest source of compressed breathable gas available is pressurized air—the volume fraction of oxygen in air is 21%. A breathable gas may have a desired humidity depending on the application including, for example, humidified air. Besides air, many options for breathable gas compositions have been formulated and used in various technical arts such as SCUBA equipment, surface supplied diving equipment, recompression chambers, submarines, space suits, spacecraft, medical life support and first aid equipment, high-altitude mountaineering and anaesthetic machines. The head cooling system may be adapted to accommodate any choice of breathable gas.

The cooled gas generator may be a vortex tube. Vortex tubes are mechanical devices that produce cold and hot air from a stream of compressed gas without needing moving parts. Vortex tubes can be useful in different applications as they are compact, simple to operate and require no electrical power or chemical input other than a compressed gas.

The interface for delivering cooled gas through a nasal orifice may be a face mask or a nasal catheter or cannula. Optionally, delivery through the nasal orifice in combination with an oral orifice may be achieved by nasal/oral cannulation.

The head cooling system may accommodate any available vortex tube. FIG. 1 shows a longitudinal cross-section view of a vortex tube 10 for illustrative purposes. The vortex tube comprises an elongate tubular body 12 defining a continuous cavity along a longitudinal axis in fluid communication with a hot gas outlet 14 and a cold gas outlet 16, respectively at opposing ends of the elongate tubular body 12. The continuous cavity running through the elongate tubular body is divided into a vortex generating chamber 18, a first section 20, and a second section 22. The vortex generating chamber 18 is substantially co-axial with and located in between the first section 20 and second section 22, the first section 20 and the second section 22 extending from opposing axial ends of the vortex generating chamber 18. The first section 20 provides a channel that extends from an opening 24 defined at a first axial end of the vortex generating chamber 18 to the hot gas outlet 14. The second section 22 provides a channel that extends from an opening 26 defined at a second axial end of the vortex generating chamber 18 to the cold gas outlet 16. The vortex generating chamber is typically located closer to the cold gas outlet 16 than the hot gas outlet 14, and accordingly the second section 22 is typically shorter than the first section 20. Opening 24 at the transition between the vortex generating chamber 18 and the first section 20 has a smaller diameter than the largest diameter of the vortex generating chamber. The first section 20 has a diameter that is substantially uniform and substantially equal to the diameter of opening 24. Opening 26 at the transition between the vortex generating chamber 18 and the second section 22 has a smaller diameter than opening 24. The second section 22 is shown in FIG. 1 to be conical expanding from the diameter of opening 26. The conical shape is not required and cylindrical versions of the second section 22 are functional.

A compressed gas inlet nozzle 28 is aligned transversely to the longitudinal axis of the elongate tubular body 12. The compressed gas inlet nozzle 28 has a first end 30 that operably connects to a compressed gas source and a second end 32 that is in fluid communication with the vortex generating chamber 18 and is aligned to direct a stream of pressurized gas tangentially along a cylindrical wall of the vortex generating chamber 18. Compressed gas enters through the inlet nozzle 28. Without wishing to be bound by theory, the gas passes through the vortex generation chamber 18 which spins the gas centrifugally along the inner cylindrical walls of the vortex generating chamber 18 and generates a first spinning gas-stream 34 that travels axially along the first section 20 at a high rate of angular velocity (eg., 1,000,000 RPM) toward the hot gas outlet 14 where a control valve allows some of the gas to escape. The remaining gas is forced back as a second spinning gas-stream 36 through the center of the first spinning gas-stream 34 travelling along the first section 20, the vortex generating chamber 18, and the second section 22 to exit as cold gas through the cold gas outlet 16. Typically, the first spinning gas-stream 34 and the second spinning gas-stream 36 will have a substantially equal angular velocity, with the first spinning gas-stream 34 having a larger diameter of rotation than the second spinning gas-stream 36. The fraction of compressed gas exiting as cold gas is often termed the Cold Fraction. The vortex tube was first discovered by a French physicist named Georges J. Ranque in 1931 and later improved by a German engineer Rudolf Hilsch in 1947. Since then, many researchers have tried to find ways to optimize its efficiency and despite having established reliable and predictable design parameters of vortex tubes there has not been a satisfactory theory to explain the radial temperature separation. Vortex tubes are typically used in cooling machine parts, cutting tools, spots under thermal stresses, electric or electronic control cabinets and food, refrigeration, solidifying polymers, liquefying natural gas, separating mixed gases and controlling air climate.

Figure 2:
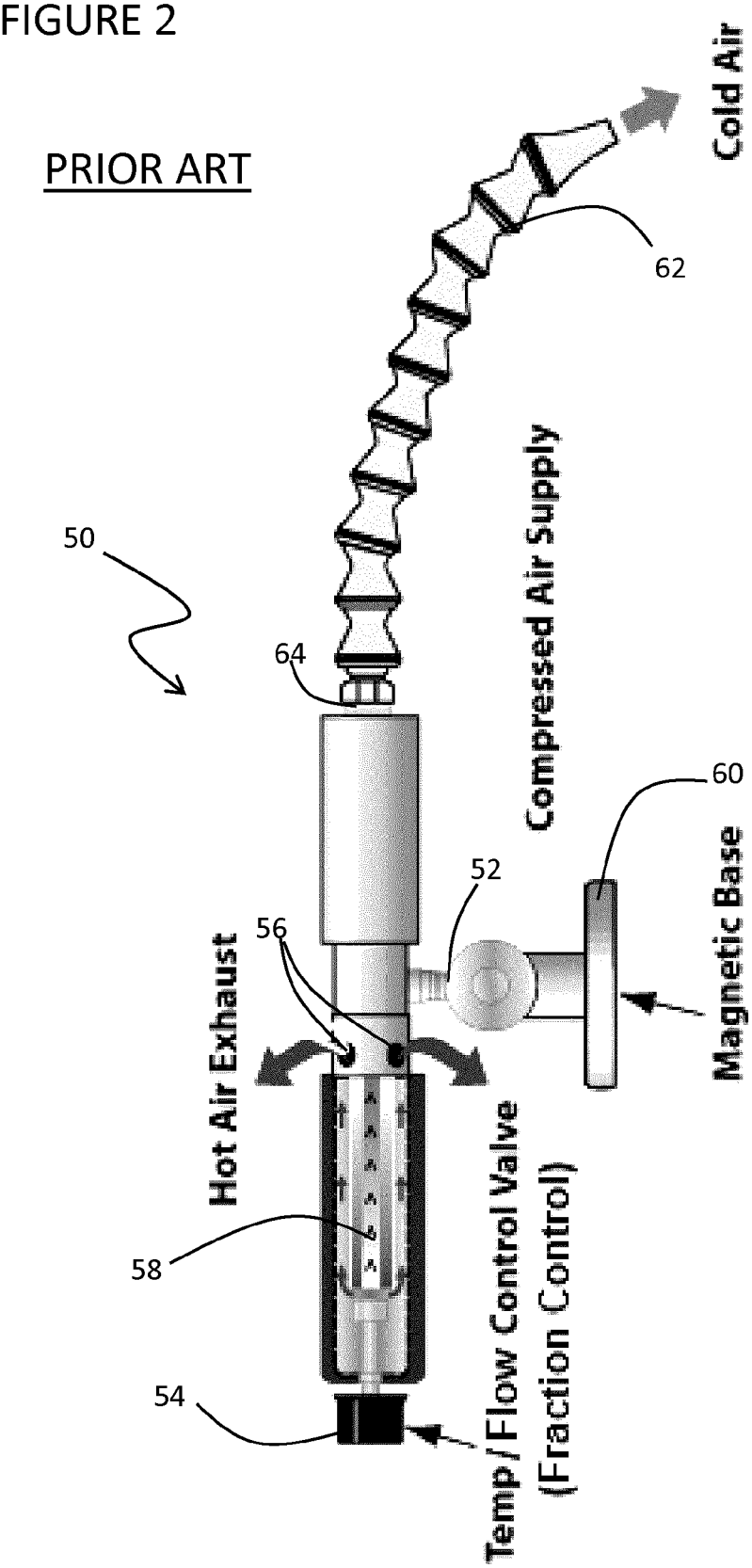
FIG. 2 shows a variant vortex tube.

FIG. 2 shows a variant vortex tube 50 that is adjustable. The vortex tube 50 divides high pressure compressed gas entering through inlet nozzle 52 into two low pressure streams, one hot and one cold, adjustable by turning the fraction control valve 54 which allows hot gas to flow through a muffling sleeve and out a hot gas exhaust 56 while the cold gas-stream 58 is also muffled and discharges through a flexible outlet hose 62 operably connected to a cold gas outlet 64 of the vortex tube 50. The vortex tube 50 is coupled to a swivel magnetic base 60 that provides easy mounting and portability. The temperature of the cold gas-stream is positively correlated with the volume flow of the cold gas-stream. Thus, turning the fraction control valve 54 to release more hot gas decreases the volume flow and the temperature of the cold gas-stream, while turning the fraction control valve 52 to release less hot gas increases the volume flow and the temperature of the cold gas-stream.

Figure 3:
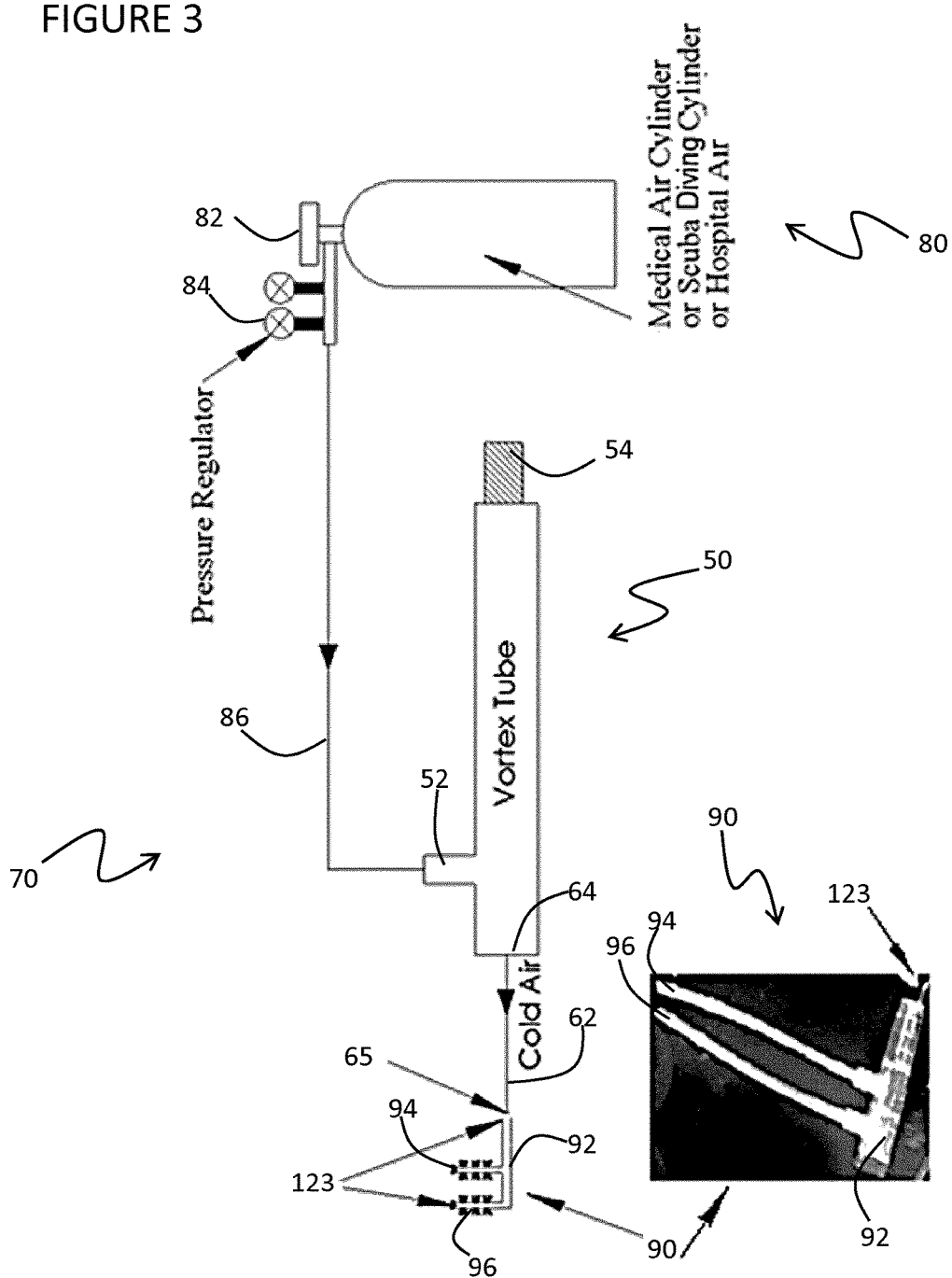
FIG. 3 shows a schematic representation of a head cooling system incorporating the vortex tube shown in FIG. 2.

FIG. 3 shows a head cooling system 70 comprising a source of compressed breathable gas 80 in fluid communication with an inlet nozzle 52 of the vortex tube 50, and a cold gas outlet 64 of the vortex tube 50 in fluid communication with a nasal cannula or catheter 90. The source of compressed breathable gas 80 includes any suitable electric compressor, tank, bottle or combinations thereof for delivering pressurized breathable gas and may optionally include features common to such sources such as an adjustable release valve 82 and/or a pressure regulator 84. An outlet of the source of compressed breathable gas 80 is operably connected to a first end of a gas delivery hose 86 with an opposing second end of the gas delivery hose 86 operably connected inlet nozzle 52 of the vortex tube 50. The cold gas outlet 64 of the vortex tube is operably connected to a first end of the flexible outlet hose 62 with an opposing second end of the flexible outlet hose 62 operably connected to the nasal catheter 90. The nasal catheter 90 comprises a tubular body 92 defining a lumen and an open end in continuous fluid communication with the flexible outlet hose 62, and first 94 and second 96 tubular nasal prongs extend from the tubular body 92. The first 94 and second 96 nasal prongs are aligned substantially parallel to each other. Each nasal prong is an elongate tube defining a longitudinal lumen and an open end opening into the lumen of the tubular body 92 and in continuous fluid communication with the lumen of the tubular body 92. Each nasal prong is typically at least about 4 centimeters in length and includes at least one aperture distal from its open end connection with the tubular body 92. The at least one aperture is communicative with the longitudinal lumen of the nasal prong. Optionally, various sensors such as temperature sensors 123 and flow rate sensors 65 may be incorporated at various locations within the head cooling system 70, for example within the nasal catheter 90 or at the cold gas outlet 64.

In operation, the first 94 and second 96 nasal prongs are each fully inserted into the nostril of a subject. The nasal catheter is fixed in place by the use of any convenient reversible fastening mechanism including, for example, straps or elastic bands for wrapping around a head or looping around ears, adhesive or double sided tape to fix the tubular body 92 at a location proximal to the nose, a nose clip and the like. Once the nasal catheter and its nasal prongs are in place the source of compressed breathable gas 80 is opened to outlet pressurized gas to the delivery hose 86. The remainder of the system may be configured to be in continuous fluid communication such that once pressurized gas begins to flow through the delivery hose 86 no further valves have to be actively opened for the pressurized gas to enter the vortex tube, be separated into a hot gas-stream and a cold-gas-stream, with the cold gas-stream flowing to the nasal catheter and exiting through the at least one aperture of each nasal prong into the nasal cavity or nasopharyngeal cavity of the subject. Optionally, any number of pressure regulators may be operably connected in communication with the gas flow path. A desired temperature of cold breathable gas exiting from the nasal prong may be achieved by selecting a suitable pressure at the outlet of the source of compressed breathable gas and/or by adjustment of fraction control valve 54 of the vortex tube 50.

The head cooling system may be easily deployed since compressed breathable gas sources such as air tanks or cylinders are readily available and can be quickly connected for operation of the system.

The head cooling system may be used in any circumstance that is characterized by neurodegeneration or a risk of neurodegeneration. For example, the system may be used by first responders such as paramedics or fire-fighters either at the scene of an emergency or within an ambulance on route to a hospital. In another example, the system may be used in hostile environments such as disaster zones or war zones to treat civilians or soldiers that have sustained a concussion or traumatic brain injury. In yet another example, the system could be used in a home setting as prophylaxis for a subject at risk of neurodegeneration, such as a risk of developing a neurodegenerative disease. Cooling the brain by 2 to 3 degrees Celsius during sleep every night may be analogous to treatment of sleep apnea with continuous positive air way pressure (CPAP) breathing machines. In a further example, the system may replace CPAP breathing machines and serve dual purposes of keeping airways open to prevent sleep apnea during sleep while providing prophylactic treatment against neurodegeneration.

The successful use of the head cooling system has been demonstrated experimentally to show localized or selective lowering of brain temperatures using various sources of compressed air as the source of compressed breathable gas and a nasal catheter or a mask as the interface for delivering cooled gas. Tests showed that delivering cooled air produced by a vortex tube into nasal cavities is an effective and simple cooling method to selectively reduce and maintain brain temperature. This method can be easily deployed inside and outside of hospital environments as it only requires a source of compressed breathable gas to operate. Furthermore, as it selectively cools the brain but not the whole body, drawbacks associated with systemic cooling may be reduced or avoided. In the following experiments the nasal prongs of the nasal catheter are each individually referred to as a nasal catheter due to the nasal cannula being custom-made by joining three separate catheters—two catheters acting as nasal prongs and a third catheter as a tubular body to connect the nasal prongs to the flexible outlet hose.

Experiments were conducted on five juvenile Duroc pigs. All animal experiments were approved by the Animal Use Subcommittee of the Canadian Council on Animal Care at The University of Western Ontario. Animals were obtained from a local supplier on the morning of the experiment. Anesthesia were induced with 3-4% isoflurane and then maintained at this level during preparatory surgery. A tracheotomy was performed and the animal was ventilated with a volume-controlled mechanical ventilator to deliver oxygen/medical air mixture (2:1). A femoral artery was catheterized to monitor heart rate (HR) and mean arterial blood pressure (MAP) and to intermittently collect arterial blood samples for gas ($p_aCO_2$, $p_aO_2$), pH and glucose analyses. Arterial $CO_2$ tension ($p_aCO_2$) was monitored throughout the experiment, either directly by blood gas or by the end-tidal $CO_2$ tension measurements, and maintained at normocapnia between 37-42 mmHg by adjusting the breathing rate and volume. Arterial oxygen tension ($p_aO_2$) was maintained at a level between 90-130 mmHg by adjusting the ratio of oxygen to medical air. Blood glucose was monitored intermittently and if it fell below 4.5 mmol/L, a 1-2 ml infusion of 25% glucose solution was administered intravenously. Rectal temperature was recorded from a rectal probe inserted to 3-4 cm from the anal margin. Deep brain temperature was also measured continuously with a thermocouple probe. A burr hole 1.5 cm posterior to the bregma along the mid-line was made in the skull with a rotary tool (Dremel tool, Robert Bosch Tool Corp.). The needle thermocouple probe was inserted through the burr hole into the brain to a depth of 2 cm from the brain surface to measure brain temperature. After surgery, each pig together with a recirculating heated water blanket were wrapped with linen blankets to keep core temperature at 38.5±0.5° C. and anesthesia was maintained on 1-2% isoflurane.

A custom-made catheter (made from Polyvinyl Chloride, PVC), coated with 2% lidocaine gel for anaesthesia and better contact with turbinates in the nasal cavity, was inserted 8-10 cm into each nostril. Nasopharygeal brain cooling was achieved by connecting the two nasal catheters to another catheter which was then connected to the cold air outlet of a commercially available vortex tube (Adjustable cold air gun, ITW Vortec Ltd). The following sources of compressed air supply to the vortex tube (VT) were tested:

I. Hospital medical air outlet at fixed inlet pressure of 50 psig (n=1);
II. Medical air cylinders with the capacity of 232 ft³ at fill-pressure of 2265 psig (supplied by L'Air Liquide Ltd) at variable VT inlet pressure of 10, 25, 35 and 50 psig (n=3);
III. Scuba (diving) cylinders with the capacity of 100 ft³ at fill-pressure of 2640 psig at VT inlet pressure of 15 and 25 psig (n=1).

In FIG. 3, the schematic of the experimental setup is shown. The cold air flow rate was set by the fraction control valve of the VT to the desired flow rates of 25 or 50 L/min as measured by a flowmeter (VWR Flowmeters Acrylic, FR4500 series with accuracy of ±3%, VWR International Inc). The temperature of air at the cold air outlet was monitored continuously with a thermometer (VWR digital thermometer with 0.1° C. precision, VWR International Inc) (FIG. 3). A thermistor was also placed inside of one of the two nasal catheters to monitor temperature of cold air inside the nasal cavity throughout the experiments. During each cooling experiment, both brain and rectal temperatures were measured every 5 min.

The efficiency of cooling with nasal catheter versus face mask was investigated in one pig. The inlet pressure was set at 25 psig while the flow rate at the cold air outlet was set to 25 L/min. Baseline brain and rectal temperature were monitored for 45-60 min until they did not change for more than 0.5° C. in 10 min., then the brain was cooled down twice first with the nasal catheters and then with a face mask with a rewarming period to baseline brain temperature between the two cooling periods.

Experiments were conducted on five juvenile pigs (4 females and 1 males), divided into three groups for testing according to Methods I, II, and III described above, with an average age of 2-3 weeks and an average weight of 14±4 kg.

Figure 4A:
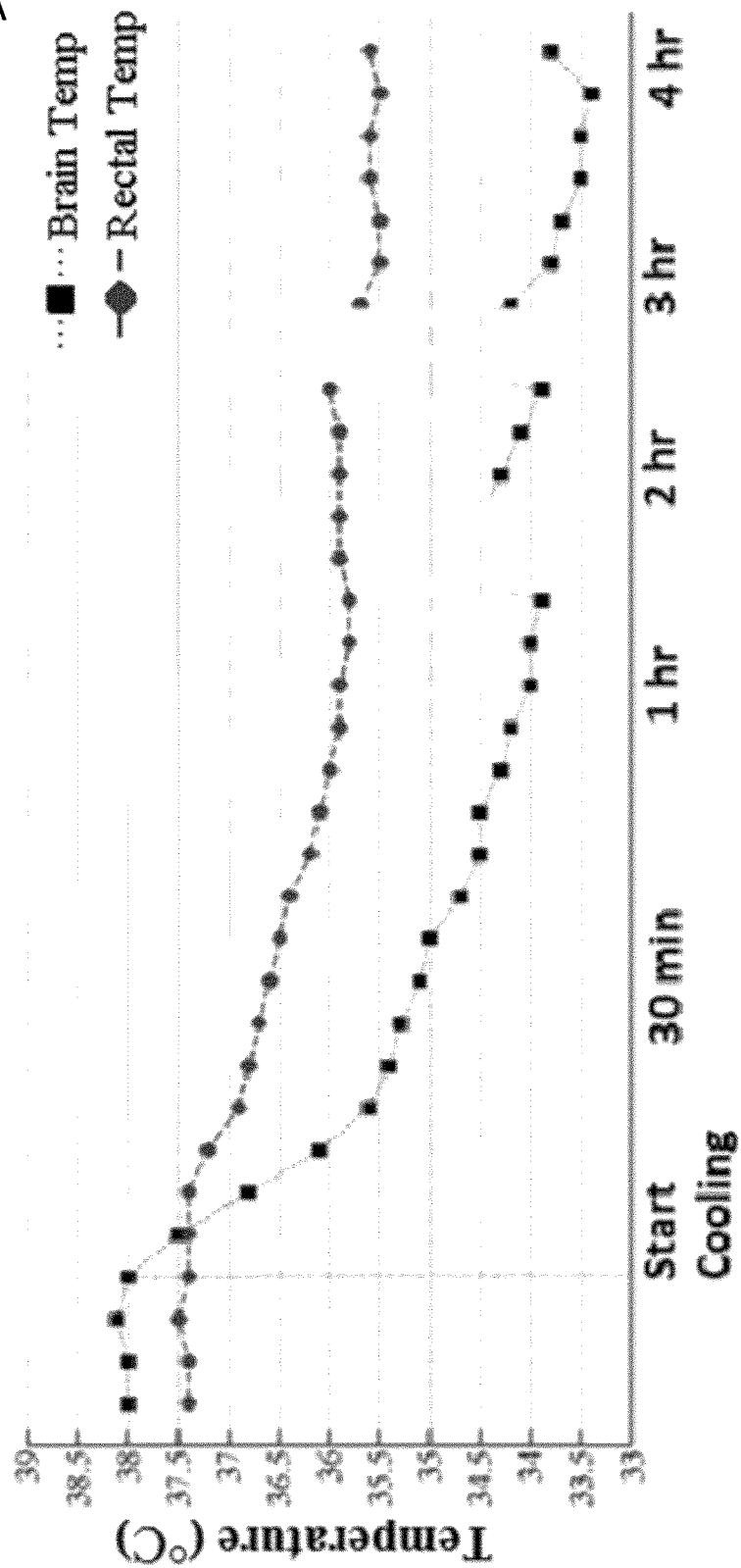
FIG. 4 shows data from a first experimental test of the head cooling system shown in FIG. 3—brain and rectal temperature over time for nasopharyngeal cooling method at a flow rate of 25 L/min and temperature of −7° C. at the cold air outlet with compressed air supplied from a hospital medical air outlet at fixed inlet pressure of 50 psig into the vortex tube (Method I) (n=1)
Figure 4B:
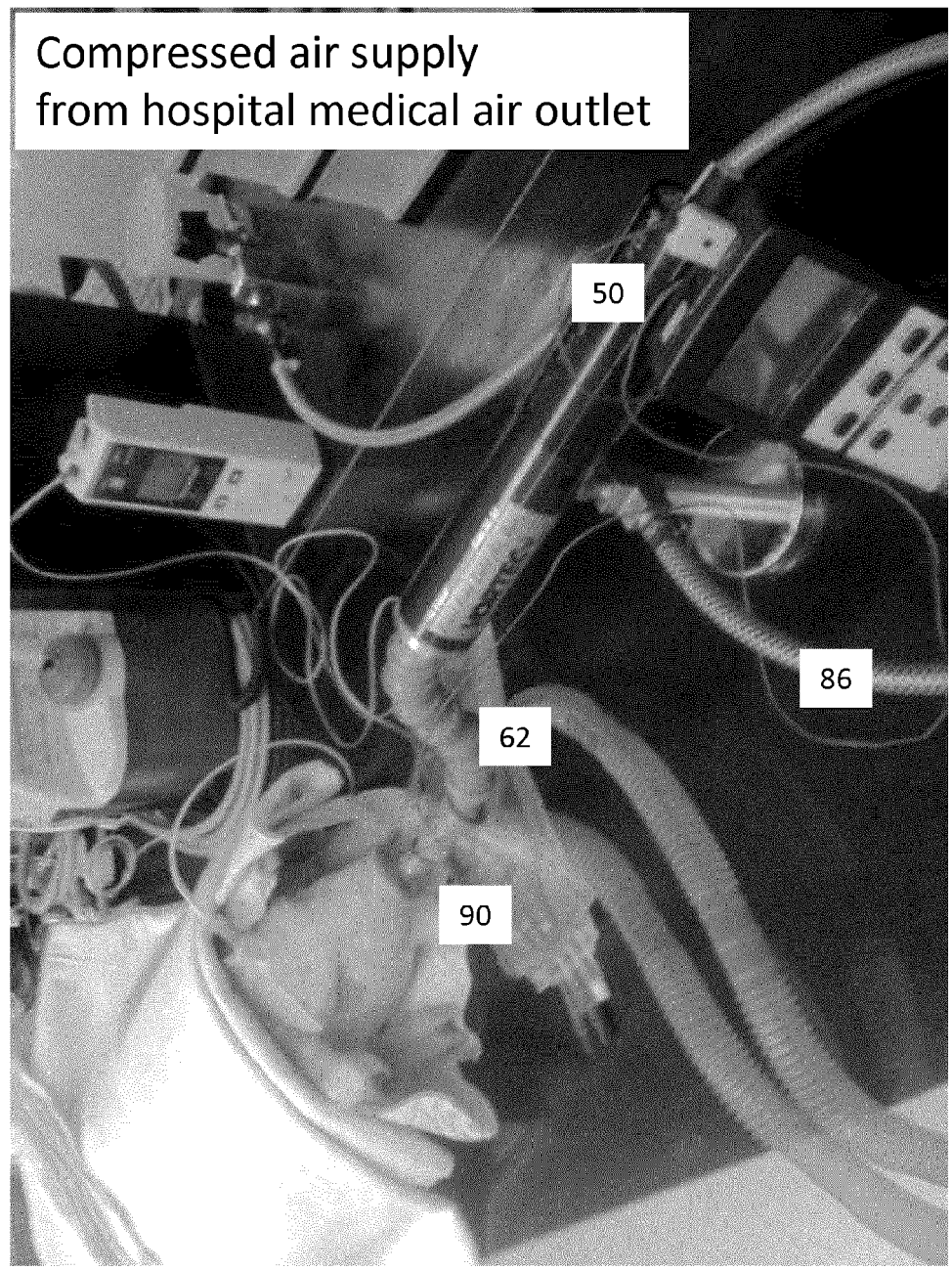

FIG. 4 demonstrates the brain and rectal temperature profile as a function of time in Method I, in which the VT was supplied with compressed air from a hospital medical air outlet at fixed inlet pressure of 50 psig. With the air flow rate of 25 L/min and temperature of −7° C. at the cold air outlet, maximum brain-rectal temperature gradient of −2° C. was reached about 45-60 min after the initiation of cooling. One hour post cooling, both brain and rectal temperatures decreased from 38° C. and 37.4° C. to 34° C. and 36° C. which corresponded to cooling rates of 4° C./h and 1.4° C./h, respectively. During the baseline monitoring period before cooling started, rectal and brain temperature relatively remained constant at 37.4±0.05 and 38±0.05, respectively.

Figure 5A:
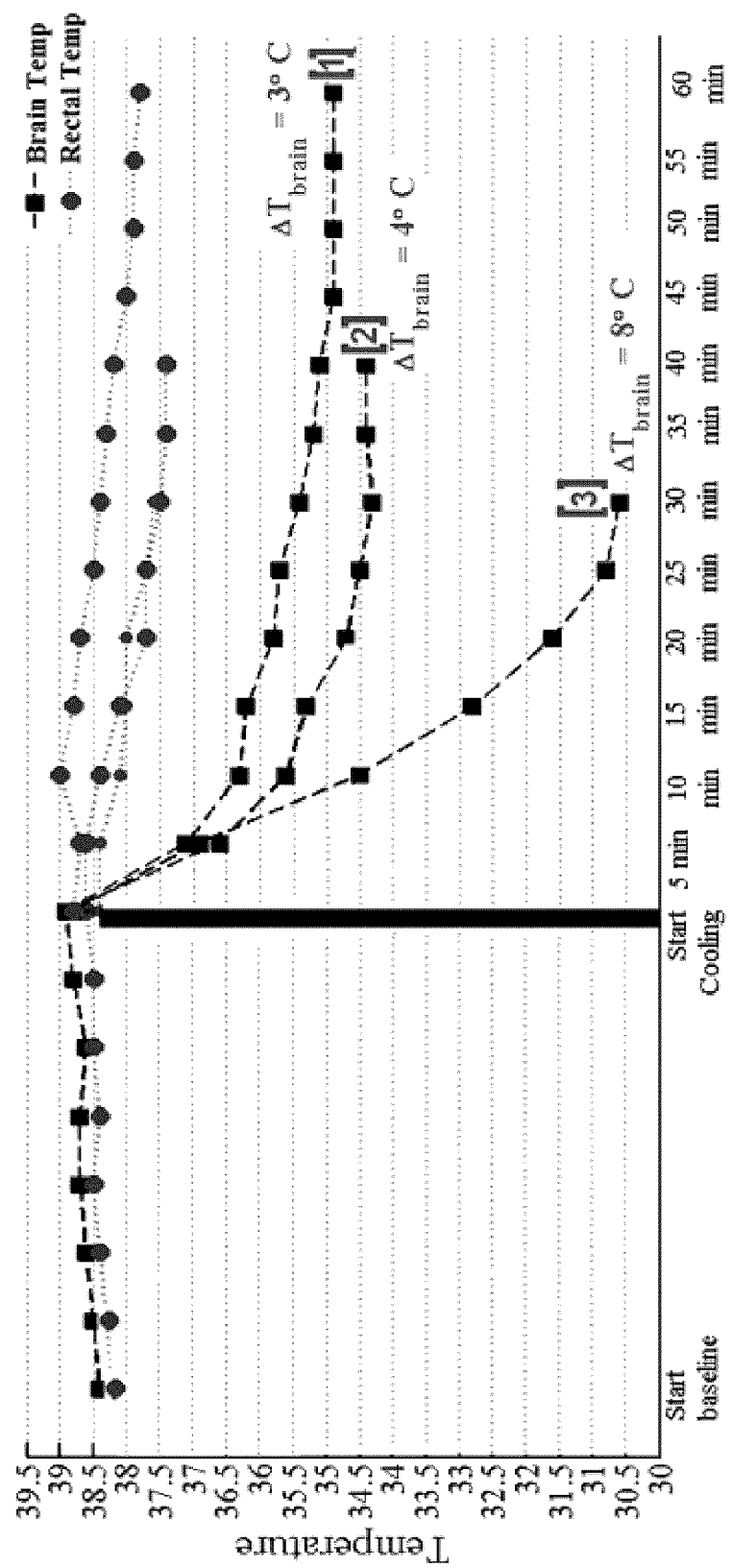
FIG. 5 shows data from a second experimental test of the head cooling system shown in FIG. 3—brain and rectal temperature over time for nasopharyngeal cooling method at a flow rate of 50 L/min and temperature of (FIG. 5A) 13±1° C.[1], −2.8±1.3° C.[2], −22±2° C.[3] and (FIG. 5B) −13.5±3° C. at the cold air outlet with compressed air supplied from medical air cylinders (Method II, FIG. 5C) at variable inlet pressure of (FIG. 5A) 10[1], 25[2] and 50[3] psig (all three conditions were applied on the same pig, n=1) (FIG. 5B) 35 psig (n=1)

By using medical air cylinders (Method II), down regulation of the inlet compressed air pressure to the VT to 10, 25 or 50 psig was set, which was much lower than the pressure within the medical air cylinders at fill-pressure of 2265 psig. This pressure drop decreased the temperature of the inlet air from that in the air cylinder via the Joule-Thomson effect; thus increasing the air cooling efficiency of the VT. At an inlet pressure of 10 psig and a flow rate of 50 L/min and a temperature of 13±1° C. at the cold air outlet, FIG. 5(a) shows that the brain-body temperature gradient reached −3° C. after 30 minutes of cooling and remained unchanged during the rest of cooling period. FIG. 5(a) also demonstrates that brain temperature could be reduced more rapidly, brain-body temperature gradient of −4° C. and −8° C. was obtained about 30 min after the initiation of cooling, at the same flow rate of 50 L/min by decreasing temperature at the cold air outlet to −2.8±1.3° C. and −22±2° C. by increasing the inlet pressure to 25 psig and 50 psig, respectively. All of the abovementioned setting for different inlet pressure were applied on the same pig (rewarming periods between the cooling episodes were not shown in FIG. 5(a)).

Figure 5B:
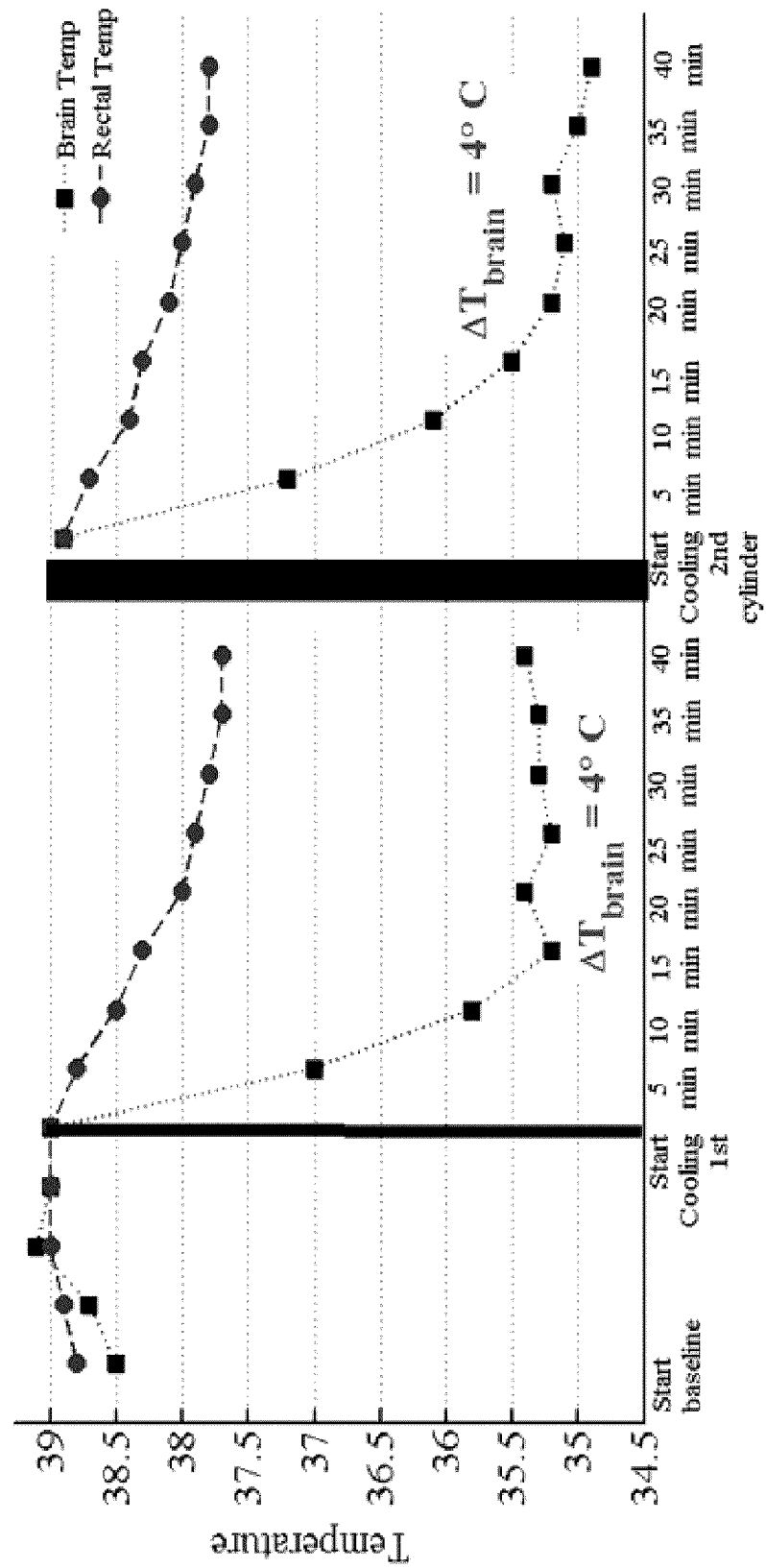

FIG. 5(b) shows the brain temperature vs time plot of two separate brain cooling episodes using the same inlet pressure of 35 psig and a flow rate of 50 L/min and a temperature of −13.5±3° C. at the cold air outlet on the same pig with a rewarming period between the two cooling periods. Following 45-60 minutes of baseline, brain temperature decreased from 39° C. to 35.2° C., corresponding to a brain-body temperature gradient of −3.8° C., within 15-20 minutes of the first nasopharyngeal cooling period. Rectal temperature continued to drop till it reached 37.7° C. at 40 min post cooling. Both brain and rectal temperature profiles were similar to that shown in FIG. 5(a) '2' demonstrating the reproducibility of the nasopharyngeal brain cooling method. The cold air input to the nasal catheters were stopped after 40 min. The temperature of the pig's brain then gradually increased till it reached the baseline temperature after an hour of rewarming. The VT was set up in the second episode of brain cooling in the same way as the first one. As shown in FIG. 5(b), no significant differences in brain and rectal temperature profiles were induced by the rewarming period between the two series of measurements obtained during nasopharyngeal brain cooling.

Figure 5C:
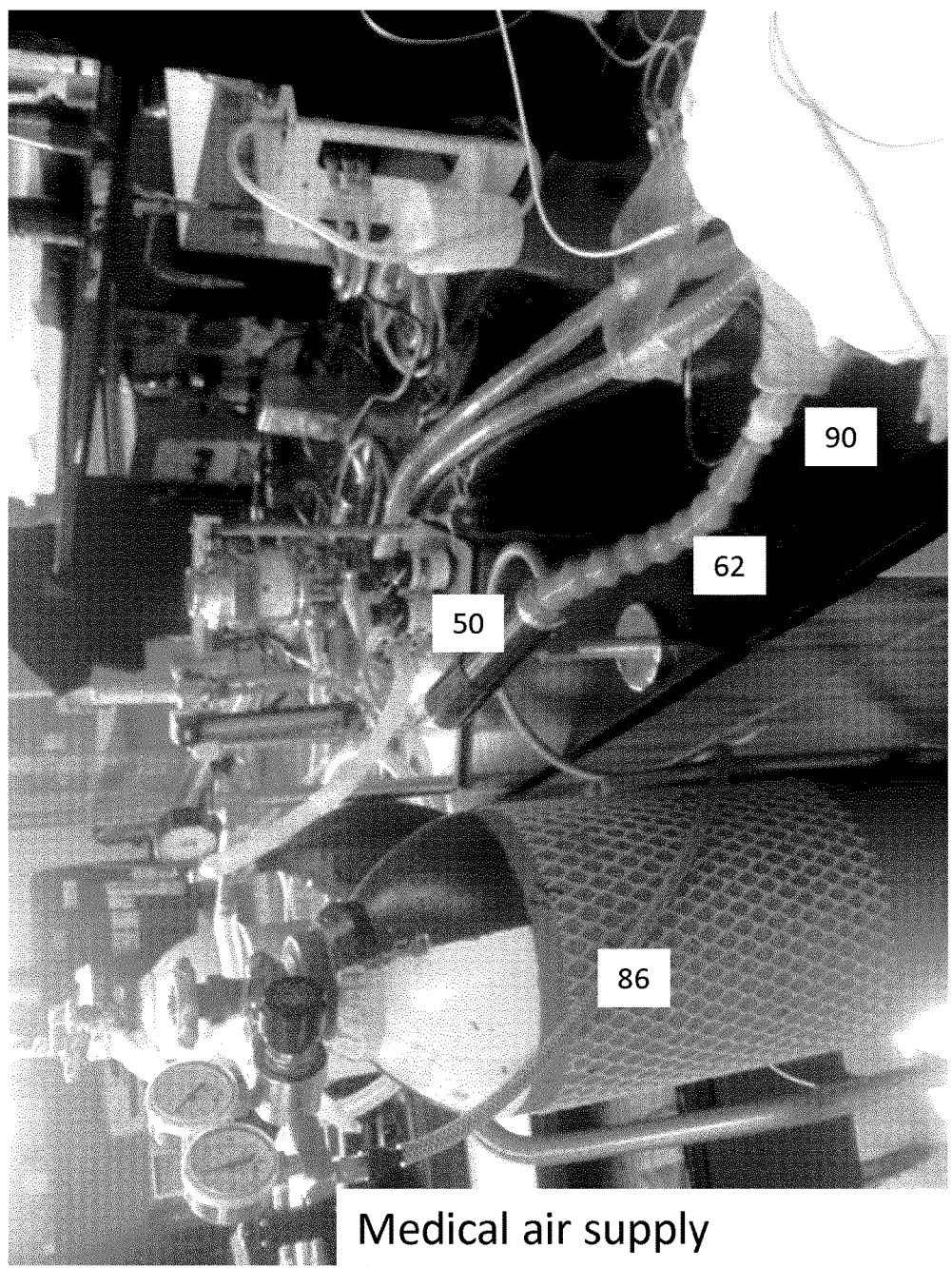
Figure 6A:
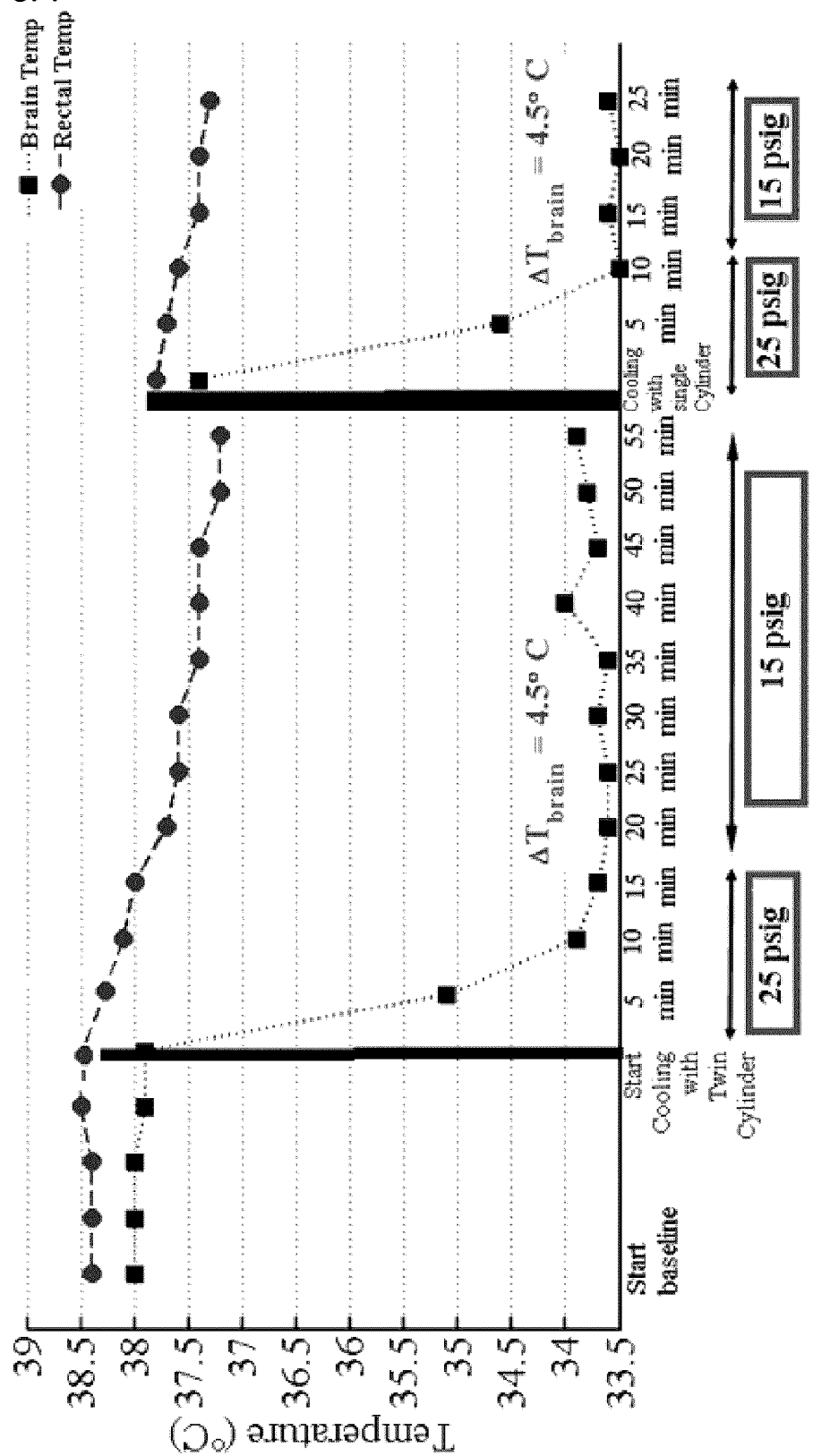
FIG. 6A shows data from a third experimental test of the head cooling system shown in FIG. 3—brain and rectal temperature over time for nasopharyngeal cooling method at a flow rate of 50 L/min with an average air temperature of 6±5° C. at the cold air outlet throughout the experiment with compressed air supplied from scuba diving cylinders (Method III, FIGS. 6B and 6C) at inlet pressure of 25 and 15 psig (n=1)
Figure 6B:
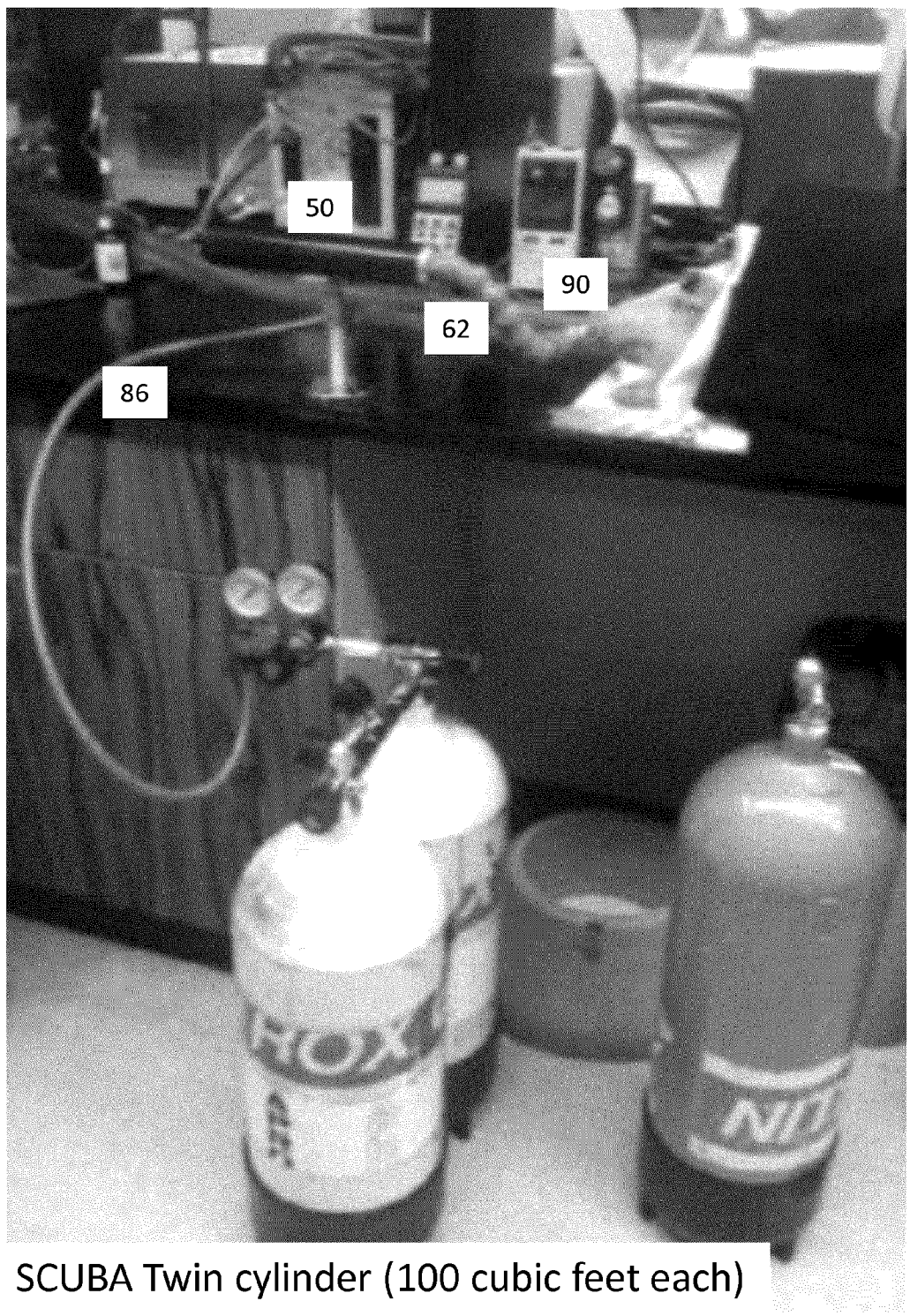
Figure 6C:
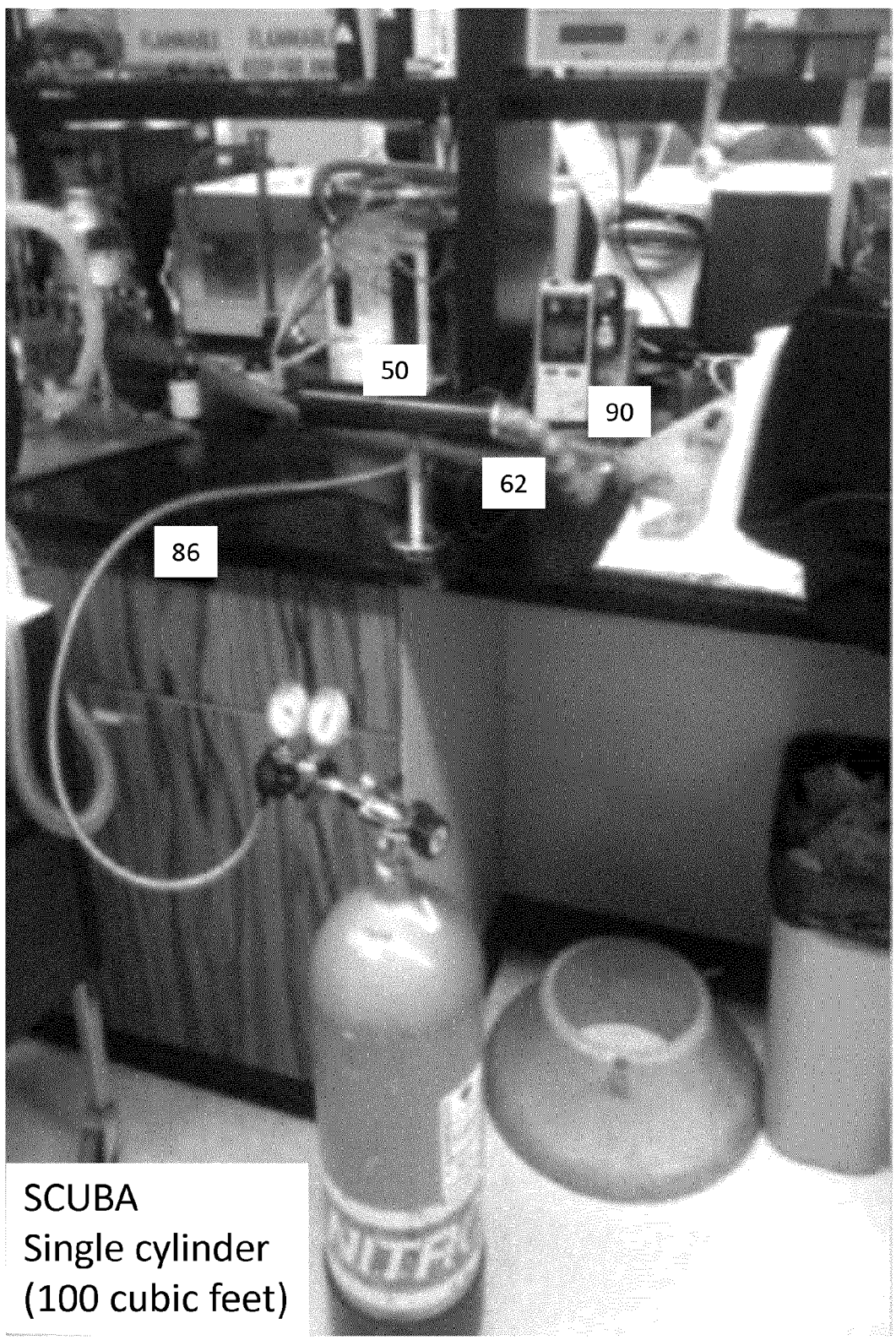
Figure 7A:
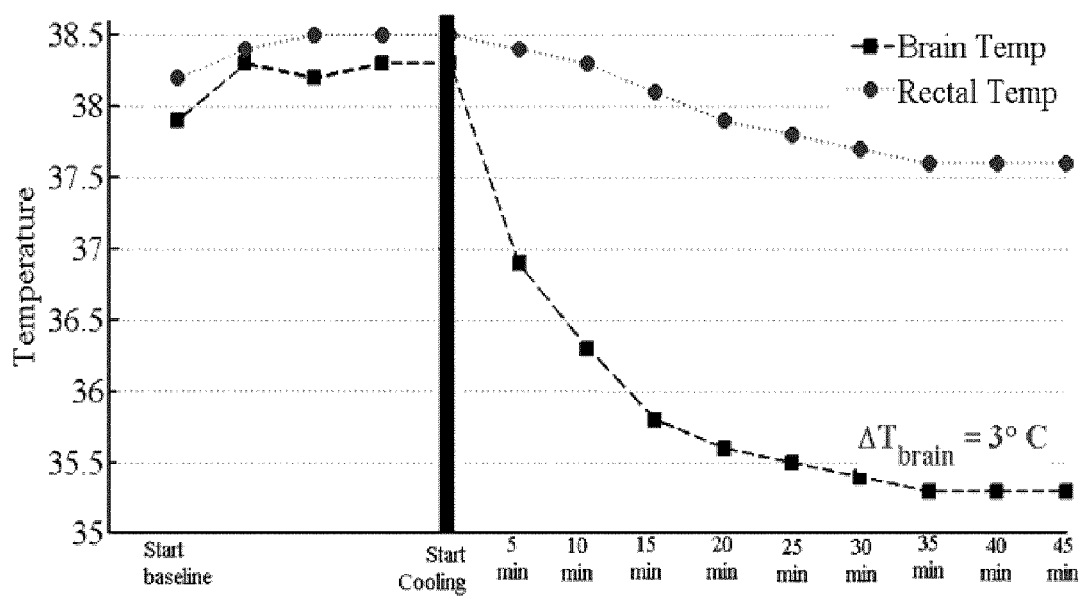
FIG. 7 shows data from a fourth experimental test of the head cooling system shown in FIG. 3—brain-rectal temperature over time for nasopharyngeal cooling using (a) nasal catheters and (b) a face mask—at a cold air flow rate of 25 L/min and average air temperature at cold air outlet of −7.5±2° C. with compressed air supplied from a medical air tank at an inlet pressure of 25 psig (n=1)
Figure 7A:
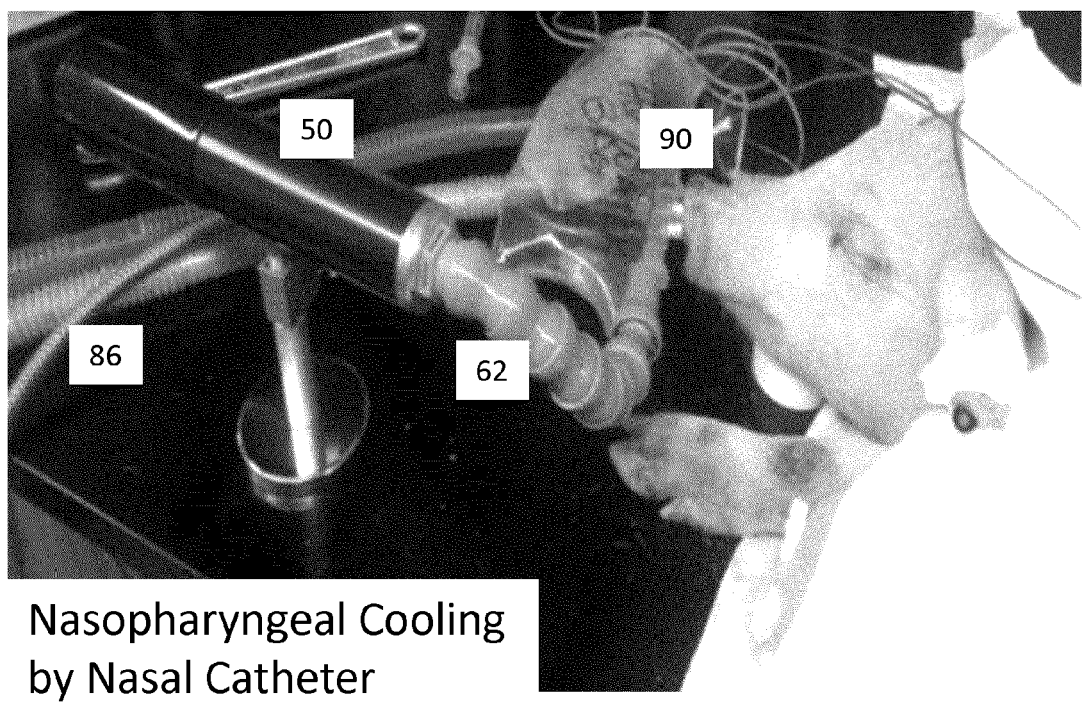
Figure 7B:
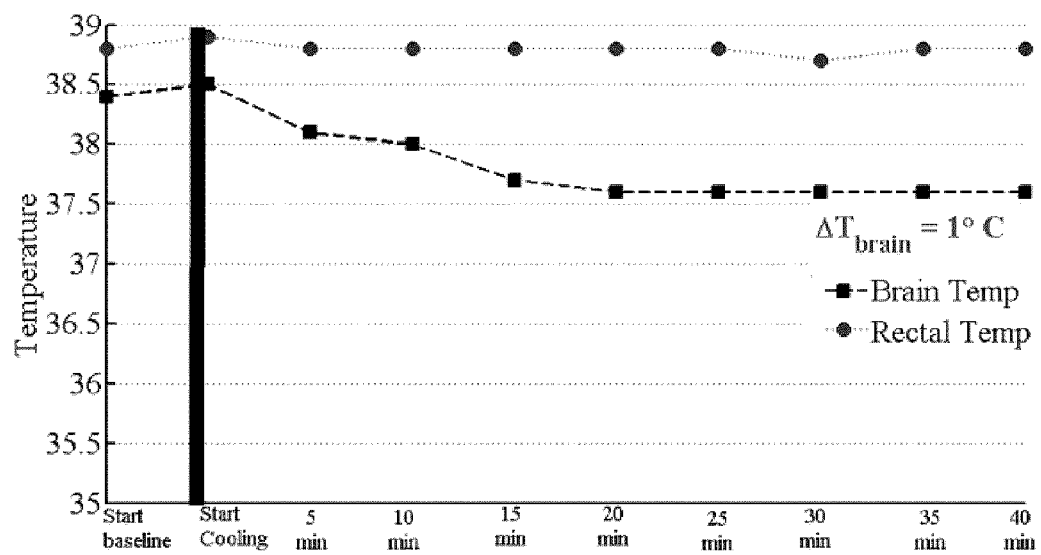
Figure 7B:
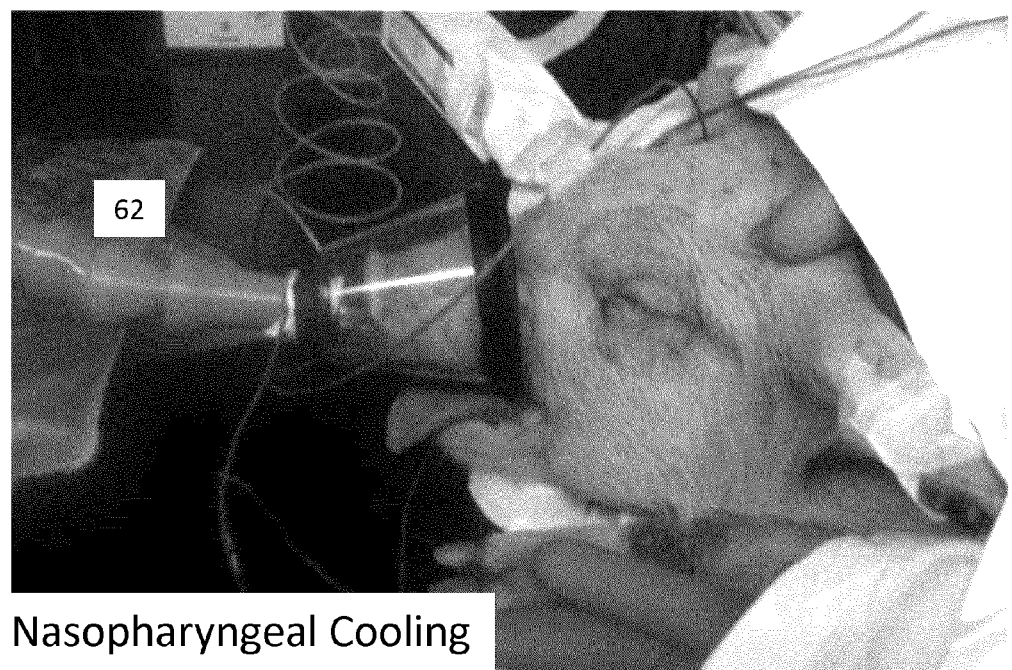

FIG. 6 displays the nasopharyngeal cooling approach using single or twin scuba diving cylinders, each has a capacity of 100 ft³ at fill-pressure of 2640 psig (Method III). The VT was set up to have an inlet pressure of 25 psig and 50 L/min and −3° C. at the cold air outlet. As before (FIG. 5), the brain temperature decreased to the 33.5° C. within 10-20 minutes of cooling. At that time the inlet pressure was decreased to 15 psig and the temperature at the cold air outlet increased to 6±3° C. These new operating conditions of the VT were able to maintain the brain temperature at ~33.5° C. for another 15 minutes (single cylinder) or 35 minutes (twin cylinders). Brain and rectal temperature decreased from 38° C. and 38.5° C. to 34° C. and 37.2° C. which corresponded to cooling rates of ≈4° C./h and ≈1.3° C./h, respectively. During the baseline monitoring period, brain and rectal temperatures variations were the same (brain: 0.1° C.; rectal: 0.1° C.).

Results of comparing nasopharyngeal cooling via catheter or mask shown in FIG. 7, reveal that brain cooling rate was greater, under the same cooling conditions, when nasal catheters were used as compared with the mask (−3° C. in 35 min vs −1° C. in 25 min). The advantage of the catheter over the mask is a surprising and useful finding.

Figure 8A:
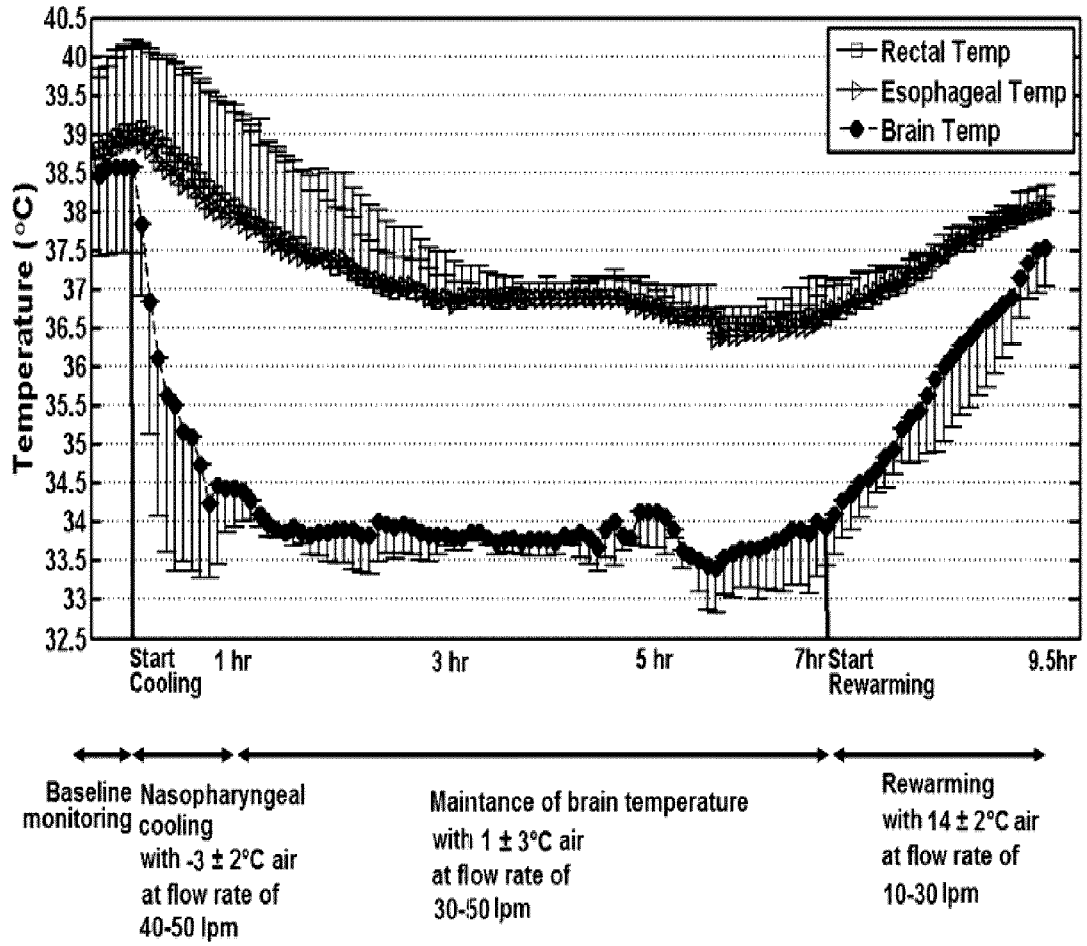
FIG. 8 shows data from a fifth experimental test using a computer-automated variant of the head cooling system shown in FIG. 3—(a) brain, rectal and esophageal temperatures over time during baseline, cooling and rewarming phases, (b) coronal cerebral blood flow maps of the same coronal, 5 mm thick slice of a pig brain at baseline, during cooling and at rewarming (n=3) and (c) a schematic representation of experimental setup.
Figure 8B:
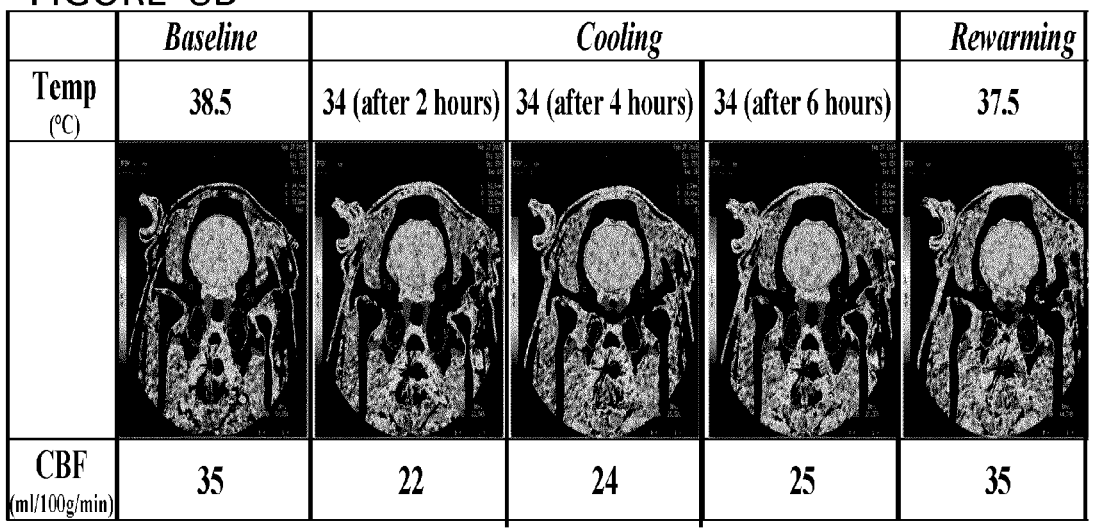

FIG. 8 and Table 1 show data from a fifth experimental test using a computer automated variant of the head cooling system shown in FIG. 3. The experimental design for the fifth experimental test was similar to the design for the first through fourth experimental tests.

Specifically, experiments were conducted on three juvenile Duroc×Landrace crossbred pigs, approximately 2-3 months old with a weight of 29 kg±4 kg. All animal experiments were approved by the Animal Use Subcommittee of the Canadian Council on Animal Care at Western University. Pigs were anesthetized with 3-4% isoflurane during preparatory surgery. The animal was intubated with a cuffed endotracheal tube and ventilated with a volume-controlled mechanical ventilator to deliver oxygen/medical air mixture (2:1). A femoral artery was catheterized to monitor heart rate (HR) and mean arterial blood pressure (MAP) and to intermittently collect arterial blood samples for gas and electrolyte levels ($p_aCO_2$, $p_aO_2$, $S_aO_2$, $cNa^+$, $cK^+$, $cCl^-$ and $cCa^{2+}$), pH and glucose analysis. A cannula was inserted into an ear vein for infusion of propofol (AstraZeneca Pharmaceuticals, Canada Inc). Arterial $CO_2$ tension ($p_aCO_2$) was monitored throughout the experiment, either directly by blood gas measurements or by the end-tidal $CO_2$ tension, and maintained at normocapnia between 37-42 mmHg by adjusting the breathing rate and volume. $EtCO_2$, tidal volume, respiratory rate, pulse oximetry ($SpO_2$) and HR were continuously measured using a multi-parameter monitor (Surgivet Advisor Vital Signs Monitor V9200, Smiths Medical, Dublin, Ohio USA). Blood glucose was monitored intermittently and if it fell below 4.5 mmol/L, a 1-2 ml infusion of 25% dextrose solution was administered intravenously. Venous blood was also collected from a right jugular vein to monitor the levels of blood gas. Arterial and venous blood gases were measured every hour during cooling and maintaining phases, by blood gas analyzer (ABL80 FLEX CO-OX, Radiometer medical ApS, DK-2700, Brønshøj, Denmark) and maintained within the normal range during the experimental period.

Body temperature was measured continuously using an esophageal probe and a rectal temperature probe attached to the same Surgivet monitor (Temperature probe WWV3418, Smiths Medical, Dublin, Ohio USA). Brain temperature was also measured continuously and invasively with a thermocouple probe. A 15-mm burr hole was drilled in the skull 1.5 posterior and 1.5 lateral to the bregma along the mid-line with a Dremel tool. The needle thermocouple probe was inserted through the burr hole into the brain to a depth of ≈2 cm from the brain surface to measure brain temperature.

Following surgery, each pig was placed prone in a light speed 64-slice computed tomography (CT) scanner (GE Healthcare, Waukesha, Wis., US) and wrapped together with a recirculating heating pad with a linen blanket. Anesthesia was maintained by ventilation with isoflurane (0.5-1.5%) and intravenous infusion of propofol (30-50 ml/hr). A period of at least of 30-45 minutes was allowed for stabilization of physiological conditions before nasopharyngeal cooling was initiated with the head cooling system. For isoflurane concentration and propofol (10 mg/ml) infusion, the rate was adjusted according to the change in vital signs such as blood pressure, HR, electrolyte levels and pain responsiveness of the pig.

After a stabilization period, brain nasopharyngeal cooling was initiated by blowing cold air (−3° C.±2) at a flow rate of 40-50 L/min into both nostrils for 50-60 min. Once the brain temperature stabilized at the target temperature of 34° C.±1° C. as measured by the intracranial thermocouple, the flow rate and air temperature were adjusted to maintain the target temperature for 6 hours while core body temperatures (i.e., rectal and esophageal temperatures) were maintained above 36.5° C. using the recirculating hot water pad and by packing gloves filled with hot water around the body of the pig within the linen blanket. After 6 hours of cooling, the temperature of the brain was allowed to gradually return to the baseline temperature in 2.5 hr. Each experiment was completed within 13-14 hours and the animal was sacrificed with intravenous potassium chloride (1-2 ml/kg, 2 mEq/mL) infusion.

Each computed tomography (CT) cerebral blood flow (CBF) measurement began with a scout CT scan to choose the locations of the CT slices. Following the baseline (normothermia) measurement, repeat CT CBF scans were collected every 2 hours throughout the cooling and rewarming period. To measure CBF, each pig received a 1.0-mL/kg injection of the iodinated contrast agent iohexol (370 mg I/mL; Isovue™, GE Healthcare, Waukesha, Wis.), at a rate of 3.0 mL/s into the Cephalic vein. Sequential (dynamic) CT scans were acquired using 80 kVp, 190 mA with the scanner once every second, for a period of 40 s. Each scan provided eight contiguous 5 mm thick coronal slices with a 12 cm field of view set to encompass the entire head of the pig. CBF maps were generated from the set of serial images using CT Perfusion software. Using an in-house software package developed in the IDL Development Environment (ITT Visual Information Solutions, Boulder, Colo.), regions of interest (ROIs) were manually drawn to encompass the whole brain on each of the CBF maps to read out the average CBF within the ROIs.

Figure 8C:
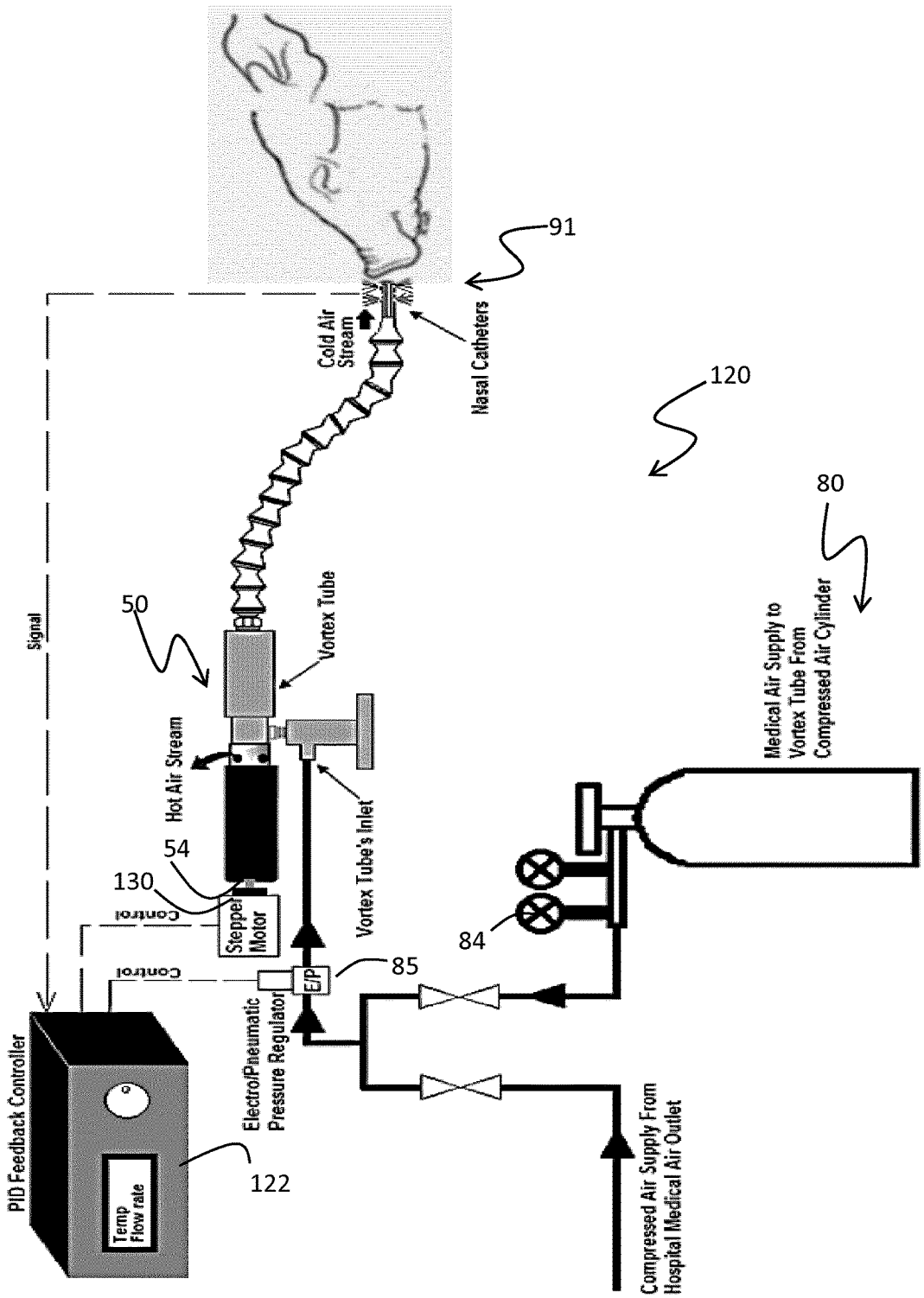

The vortex tube 50 (Adjustable cold air gun, ITW Vortec Ltd), shown in FIG. 8(c), is a mechanical device that is used to generate cold air without any moving parts, chemical reactions or external energy supply. A source of compressed medical air 80 (supplied either by L'Air Liquide Ltd in cylinders of capacity of 232 ft³ at fill-pressure of 2265 PSI down regulated to 50 PSI or from a hospital medical outlet at fixed outlet pressure of 50 PSI) is applied to the inlet nozzle of the electro pneumatic pressure regulator 85 (PULSTRONIC II series 605, Numatics Inc) to monitor and precisely regulate the pressure of the compressed air entering the vortex tube. Then air passes through the generation chamber of the Vortex tube which creates the vortex inside the tube and separates the compressed air stream into cold and hot streams. The fraction of compressed air exiting as cold air (also referred as cold fraction) was adjusted by a throttle needle fraction control valve 54 using a stepper motor 130 (IMDE17-M Integrated Motor/Driver, RMS Technologies Inc, NV, USA). Both temperature and flow rate of the cold air stream is controlled and monitored continuously by a microprocessor based digital controller 122 that includes a feedback loop (Atmel's AVR Microcontroller, ATmega64A 8-bit with 64K bytes in-system programmable flash). It automatically regulates the inlet pressure and fraction ratio based on the cold output temperature of the vortex tube to arrive at the desired setting (flow rate of 15 L/min and air temperature of −7° C.) without manual operator intervention. Moreover, temperature at the cold air outlet was monitored and recorded continuously with a thermometer (Thermometer/Data Logger, HH309A, with Four Type K Thermocouple Inputs, Omega Engineering, Stamford Conn.; resolution 0.1° C./0.1° F.). A thermistor was also placed inside one of the two nasal catheters to monitor temperature of cold air inside the nasal cavity throughout the experiments.

Table 1 displays a summary of the measured physiological parameters ($S_vO_2$, $S_aO_2$, $P_vO_2$, $P_aO_2$, $cNa^+$, $cK^+$, $cCl^-$, $cCa^{2+}$, MAP, HR, pH, $P_aCO_2$ and tHb) prior to and during cooling and during rewarming. The heart rate dropped slowly after the induction of nasopharyngeal cooling for two hours from 139±10 to 92±15 and then stabilized for the rest of the cooling period; but started to increase following rewarming albeit did not reach the heart rate prior to cooling. No instances of arrhythmia were noted during the cooling or rewarming phases. Other measured physiologic parameters were stable and within normal limits through the cooling and rewarming phase of the experiment.

(brain: 38.6° C.±1.1° C.; rectal: 38.9° C.±1.1° C.; esophageal: 38.8° C.±1.1° C.). Following 40-60 minutes of baseline, nasopharyngeal cooling was initiated with −3° C.±1° C. air at a flow rate of 40-50 L/min. The decrease in brain temperature was biexponential, it dropped rapidly to 35.6° C.±2.1° C. within 15 min. and then for the rest of 30-45 minutes within the first hour of brain cooling, the brain temperature decreased more slowly and stabilized despite further cooling with the cold air. One hour into the cooling phase, the brain temperature was 34.4° C.±0.4° C. which resulted in a mean brain cooling rate of 4.2° C./h±0.8° C./h, as displayed in FIG. 8(*a*). The rectal and esophageal temperatures decreased during the same interval from 39.1° C.±1.1° C. and 38.9° C. ±1.1° C. to 38.1° C.±1.2° C. and 37.9° C.±1.4° C., respectively—which corresponded to cooling rates of 1.1° C./h±0.2° C./h and 1.1° C./h±0.1° C./h, respectively. The brain temperature could be maintained at 34.4° C.±0.4° C. for another 6 hours by increasing the air temperature to 1° C. ±3° C. and adjusting the flow rate to 30-50 L/min, while both esophageal and rectal temperatures were maintained above 36.7° C.±0.3° C. As shown in FIG. 8(*a*), after the brain temperature stabilized at 34.4° C.±0.4° C., the esophageal and rectal temperatures continued to decrease for another 2 hours before stabilizing at 36.8° C.±0.3° C.

The brain-body temperature gradient, calculated as the difference between brain and rectal temperature, peaked at 3.9° C.±0.3° C. about 45 min after the initiation of cooling and stabilized at 3.1° C.±0.1° C. three hours into cooling.

After 7 hours of cooling, rewarming was initiated with the combined use of recirculating hot water pad, packing hot water gloves around the body of the pig and blowing 14° C.±2° C. air at a flow rate of 10-30 L/min into the nostrils. During this phase, the brain and rectal temperatures increased by 1.7° C./h±0.2° C./h and 1.3° C./h±0.2° C./h, respectively. No difference was found in the rewarming rate for either rectal temperature or esophageal temperature.

FIG. 8(*b*) shows CBF maps for the same coronal, 5 mm thick brain slice of a pig and the ROI used to calculate the

TABLE 1

Physiological parameters measured at different brain temperatures during selective brain cooling.

| | Baseline | Cooling & Maintenance phase | | | | | | Rewarming phase | | |
|---|---|---|---|---|---|---|---|---|---|---|
| | 1-45 min | 1 hr | 2 hr | 3 hr | 4 hr | 5 hr | 6 hr | 1 hr | 2 hr | 2.5 hr |
| Brain Temp (° C.) | 38.4 ± 0.8 | 34.8 ± 0.8 | 33.9 ± 0.2 | 34.0 ± 0.2 | 33.8 ± 0.2 | 34.0 ± 0.4 | 33.6 ± 0.3 | 34.8 ± 0.4 | 36.1 ± 0.2 | 37.6 ± 0.3 |
| $S_vO_2$ (%) | 91 ± 1 | 94 ± 6 | 93 ± 6 | 92 ± 1 | 89 ± 9 | 90 ± 8 | 93 ± 6 | 94 ± 5 | 95 ± 3 | 94 ± 4 |
| $P_vO_2$ (mmHg) | 61 ± 1 | 66 ± 11 | 65 ± 11 | 64 ± 14 | 60 ± 16 | 62 ± 18 | 66 ± 19 | 66 ± 12 | 67 ± 8 | 63 ± 17 |
| $S_aO_2$ (%) | 100 | 100 | 100 | 100 | 100 | 100 | 100 | 100 | 100 | 100 |
| $P_aO_2$ (mmHg) | 228 ± 66 | 262 ± 18 | 266 ± 17 | 275 ± 16 | 284 ± 25 | 274 ± 22 | 257 ± 25 | 248 ± 15 | 243 ± 8 | 240 ± 12 |
| $cNa^+$ (mmol/L) | 140 ± 1 | 139 ± 1 | 138 ± 2 | 138 ± 2 | 139 ± 2 | 138 ± 2 | 139 ± 2 | 139 ± 1 | 138 ± 2 | 138 ± 2 |
| $cK^+$ (mmol/L) | 4.5 ± 0.4 | 4.8 ± 0.1 | 5.1 ± 0.3 | 5.2 ± 0.2 | 5.0 ± 0.1 | 4.8 ± 0.6 | 4.8 ± 0.5 | 4.6 ± 0.8 | 5.2 ± 0.7 | 5.2 ± 0.6 |
| $cCa^{2+}$ (mmol/L) | 1.3 | 1.3 | 1.3 | 1.3 | 1.3 | 1.3 | 1.3 | 1.3 | 1.3 | 1.3 |
| $cCl^-$ (mmol/L) | 102 ± 2 | 100 ± 2 | 100 ± 1 | 101 ± 1 | 102 ± 2 | 100 ± 2 | 101 ± 2 | 101 ± 3 | 100 ± 2 | 101 ± 2 |
| MAP (mmHg) | 94 ± 1 | 85 ± 12 | 72 ± 5 | 76 ± 2 | 82 ± 4 | 75 ± 5 | 67 ± 2 | 66 ± 1 | 66 ± 2 | 69 ± 3 |
| HR (bpm) | 139 ± 10 | 124 ± 25 | 92 ± 15 | 86 ± 17 | 90 ± 14 | 85 ± 9 | 87 ± 10 | 90 ± 4 | 92 ± 6 | 95 ± 5 |
| Ph | 7.5 | 7.5 | 7.5 | 7.5 | 7.5 | 7.5 | 7.5 | 7.5 | 7.5 | 7.5 |
| tHb (g/dL) | 9.6 ± 0.3 | 9.4 ± 0.4 | 9.5 ± 0.8 | 9.2 ± 0.4 | 9.1 ± 0.5 | 8.4 ± 1.1 | 8.9 ± 0.8 | 8.9 ± 0.8 | 8.8 ± 0.6 | 9.0 ± 0.6 |
| $P_aCO_2$ (mmHg) | 39 ± 1 | 38 ± 1 | 37 ± 2 | 40 ± 1 | 38 ± 1 | 39 ± 2 | 38 ± 3 | 41 ± 2 | 40 ± 2 | 41 ± 1 |

$S_vO_2$—Oxygen saturation of venous blood (from jugular vein); $S_aO_2$—Oxygen saturation of arterial blood; $P_aO_2$—partial pressure of oxygen in arterial blood; $cNa^+$—sodium concentration in arterial blood; $cK^+$—potassium concentration in arterial blood; $cCa^+$—calcium concentration in arterial blood; $cCl^-$—chloride concentration in arterial blood; MAP—mean arterial pressure; HR—heart rate; tHb—total hemoglobin concentration in arterial blood; $P_aCO_2$—partial pressure of carbon dioxide in arterial blood.

Average rectal and brain temperatures for the three pigs studied in the fifth experimental test are shown in FIG. 8(*a*). During baseline monitoring, mean brain and core body temperatures did not decrease more than 0.2° C.±0.1° C.

average CBF within the slice at different brain temperatures. As brain temperature decreased from baseline (38.5° C.) to 34° C., CBF also decreased from 35 ml. $min^{-1}.100$ $g^{-1}$ to 22-25 ml. $min^{-1}.100$ $g^{-1}$. CBF remained relatively stable throughout the rest of the cooling period, however, during rewarming phase when the brain temperature reached 37.5° C., CBF increased from 25±26 ml. min$^{-1}$.100 g$^{-1}$ to the baseline value of 35±45 ml. min$^{-1}$.100 g$^{-1}$.

FIGS. 9, 10, 11 and 12 and Table 2 show data from a sixth experimental test using a computer automated variant of the head cooling system shown in FIG. 3. The experimental design for the sixth experimental test was similar to the design for the first through fifth experimental tests.

Experiments were conducted on six male New Zealand white rabbits, approximately 6 months old (weight=3.5 kg±0.2 kg). All animal experiments were approved by the Animal Use Subcommittee of the Canadian Council of Animal Care at Western University. Animals were induced and maintained with isoflurane gas anesthesia at 4% and 2-3% concentrations, respectively. The animal was intubated with a cuffed endotracheal tube and ventilated with a volume-controlled mechanical ventilator to deliver oxygen/medical air mixture (2:1). Body temperature was measured continuously using an esophageal and a rectal temperature probe attached to a Surgivet monitor (Temperature probe WWV3418, Smiths Medical, Dublin, Ohio USA). A 1-2 mm burr hole was drilled in the skull 1.5 posterior and 1.5 lateral to the bregma along the mid-line with a Dremel tool. The needle thermocouple probe was inserted through the burr hole into the brain to a depth of ≈2 cm from the brain surface to measure brain temperature. A femoral artery was catheterized to monitor heart rate (HR) and mean arterial blood pressure (MAP) and to intermittently collect arterial blood samples for gas and electrolyte levels ($p_aCO_2$, $p_aO_2$, $S_aO_2$, $cNa^+$, $cK^+$, $cCl^-$ and $cCa^{2+}$), pH and glucose analyses.

Figure 9:
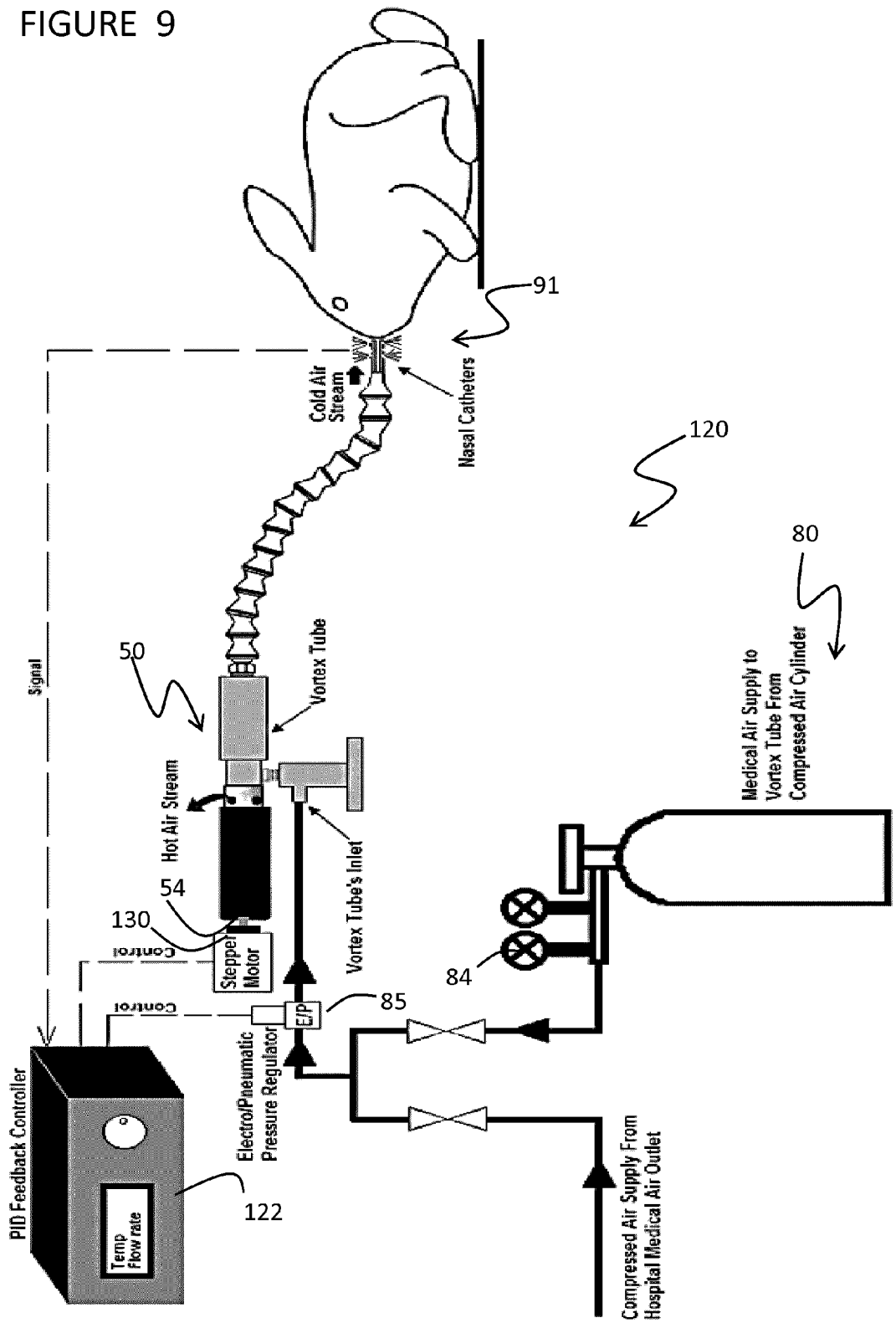
FIG. 9 shows a schematic representation of a computer-automated variant of the head cooling system shown in FIG. 3 used for nasopharyngeal cooling in a sixth experimental test.

After surgery, each animal together with a recirculating hot water pad were wrapped with linen blankets, maintained on 2-3% isoflurane, and 30-40 minutes were allowed for baseline physiological to stabilize before the nasopharyngeal brain cooling was started. Two successive experiments were performed on each animal. In the first experiment, nasopharyngeal brain cooling was initiated by blowing room temperature air, delivered from a hospital medical air outlet, at a flow rate of 14-15 L/min as measured by a flow meter (VWR Flow meters Acrylic, FR4500 series with accuracy of ±3%, VWR International Inc) into both nostrils for 60 min (Group I). The brain was then allowed to gradually rewarm to baseline temperature by turning off the hospital air supply. In the second experiment, brain cooling was accomplished by blowing cold air (−7° C.) at the same flow rate as the first experiment for 60 minutes. Once the brain temperature stabilized, the flow rate and air temperature were adjusted to maintain the brain temperature reached for another 60 minutes while core body temperature was maintained above 36° C. using the recirculating hot water pad and by packing gloves filled with old water around the body (Group II). Cold air was generated by a computer automated variant of the head cooling system as shown in FIG. 9.

Arterial $CO_2$ tension ($p_aCO_2$) was monitored throughout the experiments, either directly by blood gas measurements or by the end-tidal $CO_2$ tension ($EtCO_2$), and maintained at normocapnia between 37-42 mmHg by adjusting the breathing rate and volume. $EtCO_2$, tidal volume, respiratory rate, pulse oximetry ($SpO_2$), and heart rate were continuously measured using a multi-parameter monitor (Surgivet Advisor Vital Signs Monitor V9200, Smiths Medical, Dublin, Ohio USA). Venous blood was collected from the right jugular vein to monitor the venous blood gas measurements. Arterial blood was drawn every 30 minutes during cooling and every hour in maintaining phase to measure arterial blood gas with an analyzer (ABL80 FLEX CO-OX, Radiometer medical ApS, DK-2700, Brønshøj, Denmark).

Altogether, 12 cooling experiments were performed on six rabbits (two for each rabbit). Each experiment was completed in 7-9 hours and the animal was sacrificed with intravenous potassium chloride (1-2 ml/kg, 2 mEq/mL) infusion at the end of the experiments.

The experimental procedures used on newborn piglets were similar to those used on rabbits. Briefly, after surgery, each piglet was wrapped with linen blankets, maintained on 1-2% isoflurane, and randomized to the following nasopharyngeal brain cooling treatments: room temperature at a flow rate of 14-15 L.min$^{-1}$ (n=6); and −8±2° C. at a flow rate of 14-15 L. min$^{-1}$ (n=6). Cold air was generated by circulating air, delivered from a pressurized tank, through a custom-made heat exchanger.

SPSS 17.0.0 (SPSS, Inc, Chicago, Ill.) was used for all statistical analyses. For comparisons between groups, t test was used for Gaussian and Mann-Whitney U test for non-Gaussian distributed data. Repeated measure analysis of variance was used to compare brain temperature measurements made at different cooling times. Statistical significance was declared when p-value was <0.05. All numeric data are presented as mean±standard deviation (SD) unless otherwise noted.

The vortex tube 50 (Adjustable cold air gun, ITW Vortec Ltd), shown in FIG. 9, is a mechanical device that is used to generate cold air without any moving parts, chemical reactions or external energy supply. A source of compressed medical air 80 (supplied either by L'Air Liquide Ltd in cylinders of capacity of 232 ft$^3$ at fill-pressure of 2265 PSI down regulated to 50 PSI or from a hospital medical outlet at fixed outlet pressure of 50 PSI) is applied to the inlet nozzle of the electro pneumatic pressure regulator 85 (PULSTRONIC II series 605, Numatics Inc) to monitor and precisely regulate the pressure of the compressed air entering the vortex tube. Then air passes through the generation chamber of the Vortex tube which creates the vortex inside the tube and separates the compressed air stream into cold and hot streams. The fraction of compressed air exiting as cold air (also referred as cold fraction) was adjusted by a throttle needle fraction control valve 54 using a stepper motor 130 (IMDE17-M Integrated Motor/Driver, RMS Technologies Inc, NV, USA). Both temperature and flow rate of the cold air stream is controlled and monitored continuously by a microprocessor based digital controller 122 that includes a feedback loop (Atmel's AVR Microcontroller, ATmega64A 8-bit with 64K bytes in-system programmable flash). It automatically regulates the inlet pressure and fraction ratio based on the cold output temperature of the vortex tube to arrive at the desired setting (flow rate of 15 L/min and air temperature of −7° C.) without manual operator intervention. Moreover, temperature at the cold air outlet was monitored and recorded continuously with a thermometer (Thermometer/Data Logger, HH309A, with Four Type K Thermocouple Inputs, Omega Engineering, Stamford Conn.; resolution 0.1° C./0.1° F.). A thermistor was also placed inside one of the two nasal catheters to monitor temperature of cold air inside the nasal cavity throughout the experiments. FIG. 9 shows the schematic of the experimental setup. Nasopharyngeal brain cooling was achieved via a custom made rabbit nasal canula 91 by connecting the two nasal catheters (made from Polyvinyl Chloride, PVC) to cold air outlet of a vortex tube via a tubing. The nasal catheters were coated with 2% lidocaine gel for local anesthesia during insertion and were inserted 4-5 cm into each nostril.

Table 2 displays a summary of the measured physiological parameters ($S_vO_2$, $S_aO_2$, $cNa^+$, $cK^+$, $cCl^-$, $cCa^{2+}$, MAP, HR, pH, $P_aCO_2$ and tHb) in the two groups, prior to and during cooling. There was no significant difference in any physiological parameter between the groups at baseline. In group I, one hour post cooling when the mean brain temperature dropped to 34.5° C.±0.9° C., a statistically significant (p<0.05) decrease in HR and MAP were observed; but $cK^+$ started increasing after initiation of cooling. Similarly, in group II, there were statistically significant decreases in HR and MAP when the brain temperature dropped to 35.4° C.±0.9° C. and 33.2° C.±1.2° C. after 30 min and 1 hr of cooling, respectively, and remained significantly depressed (relative to baseline) for the duration of the study. As well, a statistically significant increase in $cK^+$ was observed after two hours of cooling. No arrhythmias were noted during cooling or rewarming.

cooling temperature was usually achieved in 80±15 min. During this phase, the brain and rectal temperatures increased by 2.9° C./hr±0.7° C./h and 1.7° C./hr±0.5° C./hr, respectively. Temperatures in the rewarming period between the cooling episodes were not shown in FIGS. 10 and 11.

Brain cooling at the rate of 3.7° C./h±0.9° C./h in rabbits was achieved by setting the flow rate of room temperature air to 14-15 L/min. The rapid temperature changes in the brain suggest that the cerebral circulation carries the cooling effect which is based on heat exchange in the cavernous sinus. This can be supported by experiments in newborn piglets using a similar nasopharyngeal technique showing approximately the same cooling rates. Similarly, in newborn piglets, with the initiation of nasopharyngeal cooling with the same setting, the brain temperature decreased to 33.9° C.±1.7° C. from baseline (38.5° C.±0.9° C.) which resulted in mean brain cooling rates of 4.6° C./h±1.2° C./h.

TABLE 2

Physiological parameters measured at different times during selective brain cooling within groups I and II.

| Variable | Group I (14-15 L/min at room temp.) | | | Group II (14-15 L/min at −7° C.) | | | |
|---|---|---|---|---|---|---|---|
| | Baseline | 30 min | 1 hr | Baseline | 30 min | 1 hr | 2 hr |
| Brain Temp (° C.) | 38.2 ± 0.7 | 35.2 ± 0.7* | 34.5 ± 0.9* | 37.8 ± 0.4 | 35.4 ± 0.9* | 33.2 ± 1.2* | 32.1 ± 1.7* |
| $S_vO_2$ (%) | 99 ± 1 | 99 ± 1 | 98 ± 2 | 96 ± 3 | 97 ± 3 | 96 ± 3 | 90 ± 8 |
| $S_aO_2$ (%) | 100.0 | 100.0 | 100.0 | 100.0 | 100.0 | 100.0 | 100.0 |
| $cNa^+$ (mmol/L) | 141 ± 3 | 142 ± 2 | 142 ± 3 | 144 ± 2 | 142 ± 1 | 141 ± 1 | 141 ± 2 |
| $cK^+$ (mmol/L) | 3.4 ± 0.3 | 3.5 ± 0.2 | 3.7 ± 0.1 | 4.4 ± 0.2 | 4.3 ± 0.5 | 4.3 ± 0.3 | 5.3 ± 0.8* |
| $cCa^{2+}$ (mmol/L) | 1.2 ± 0.1 | 1.0 ± 0.1 | 1.3 ± 0.1 | 1.1 ± 0.1 | 1.3 ± 0.1 | 1.2 ± 0.1 | 1.2 ± 0.1 |
| $cCl^-$ (mmol/L) | 102 ± 2 | 104 ± 2 | 102 ± 2 | 110 ± 3 | 104 ± 3 | 103 ± 1 | 108 ± 2 |
| MAP (mmHg) | 37 ± 6 | 34 ± 6 | 30 ± 5* | 35 ± 4 | 32 ± 7 | 27 ± 6* | 25 ± 6* |
| HR (bpm) | 272 ± 20 | 250 ± 14* | 226 ± 16* | 275 ± 11 | 247 ± 18* | 215 ± 20* | 204 ± 15* |
| pH | 7.4 ± 0.1 | 7.4 ± 0.1 | 7.4 ± 0.1 | 7.4 ± 0.1 | 7.3 ± 0.1 | 7.3 ± 0.1 | 7.3 ± 0.1 |
| tHb (g/dL) | 11.1 ± 1.0 | 12.2 ± 0.8 | 12.5 ± 1.0 | 12.4 ± 1.0 | 12.1 ± 0.3 | 12.4 ± 0.9 | 12.6 ± 0.7 |
| $P_aCO_2$ (mmHg) | 38 ± 2 | 40 ± 2 | 37 ± 2 | 37 ± 2 | 39 ± 3 | 40 ± 1 | 41 ± 2 |

MAP = mean arterial blood pressure; HR = heart rate; $S_vO_2$ = venous oxygen saturation; tHb = total hemoglobin in blood; $P_aCO_2$ = arterial oxygen partial pressure; $cNa^+$ = sodium concentration; $cK^+$ = potassium concentration; $cCa^{2+}$ = calcium concentration; $cCl^-$ = chloride concentration;
*A statistically significant (P < 0.05) difference compared to the baseline at the beginning of the experiment.

Effects of nasopharyngeal cooling with room temperature air in rectal and brain temperatures in rabbits are shown in FIG. 10(a). During baseline monitoring period of 40-60 min, both rectal and brain temperature did not vary more than 0.1° C.±0.1° C. from baseline. With the initiation of nasopharyngeal cooling with room temperature air at a flow rate of 14-15 L/min, the brain temperature decreased to 35.6° C.±0.9° C. within 15 min. One hour post cooling, the brain temperature reached 34.1° C.±1.2° C. which resulted in a mean brain cooling rate of 3.7° C./h±0.9° C./h, as displayed in FIG. 10(a). The rectal temperature decreased during the same interval from 38.1° C.±0.3° C. to 36.2° C.±0.6° C. which corresponded to a cooling rate of 1.9° C./h±0.4° C./h. FIG. 10(b) shows the brain and rectal temperature as a function of time of piglets which underwent nasopharyngeal brain cooling in the same manner as the rabbits. Both brain and rectal temperature decreased from 38.4° C.±0.7° C. and 38.2° C.±0.7° C. to 34.8° C.±1.7° C. and 35.3° C.±1.7° C. which corresponded to cooling rates of 2.6° C./h±1.1° C./h and 1.8° C./h±0.6° C./h, respectively, as displayed in FIG. 10(b).

Following 60 minutes of cooling with room temperature air at a flow rate of 14-15 L/min, the air flow was stopped and rewarming was initiated with the use of recirculating hot water pad and by packing gloves filled with hot water around the body of the animal. The return to the baseline pre- FIG. 11(a) shows that with the use of the computer automated variant head cooling system 120 providing −7° C. air instead of room temperature air at the same flow rate, a faster cooling rate was achieved in rabbits. Mean brain and rectal temperatures decreased to 32.2° C. ±2.1° C. and 36.5° C.±0.5° C. within 60 minutes of cooling from baseline temperature of 37.5° C.±0.8° C. and 38.1° C.±0.3° C., which corresponded to cooling rates of 5.2° C./hr±1.9° C./h and 1.6° C./hr±0.4° C./hr, respectively. The brain-body temperature gradient, calculated as the difference between brain and rectal temperature, peaked about 55 min after the initiation of cooling. This gradient could be maintained within ±0.5° C. for another hour by increasing the temperature to 4° C.±4° C. and adjusting the air flow rate to 20±10 L/min. Similarly in piglets, FIG. 11(b) shows that brain and rectal temperatures were reduced more rapidly at a rate of 5.6° C./hr±1.1° C./h and 3.1° C./hr±1.1° C./h by using −7° C. instead of room temperature air at the same flow rate.

In rabbits, maximum brain-rectal temperature gradient of −4.5° C. was reached about 50 minutes after the initiation of cooling and remained unchanged during the rest of nasopharyngeal cooling. However, in piglets, the rectal temperature continued to drop till it reached the cooled brain temperature. The most likely explanation for this discrepancy is that in rabbits once the brain temperature stabilized after 60 min of nasopharyngeal cooling, the core temperature was maintained >36° C. using recirculating heated water blankets and hot water gloves, however in piglets, their body was only covered with linen sheets and no external heating sources were utilized.

Figure 12:
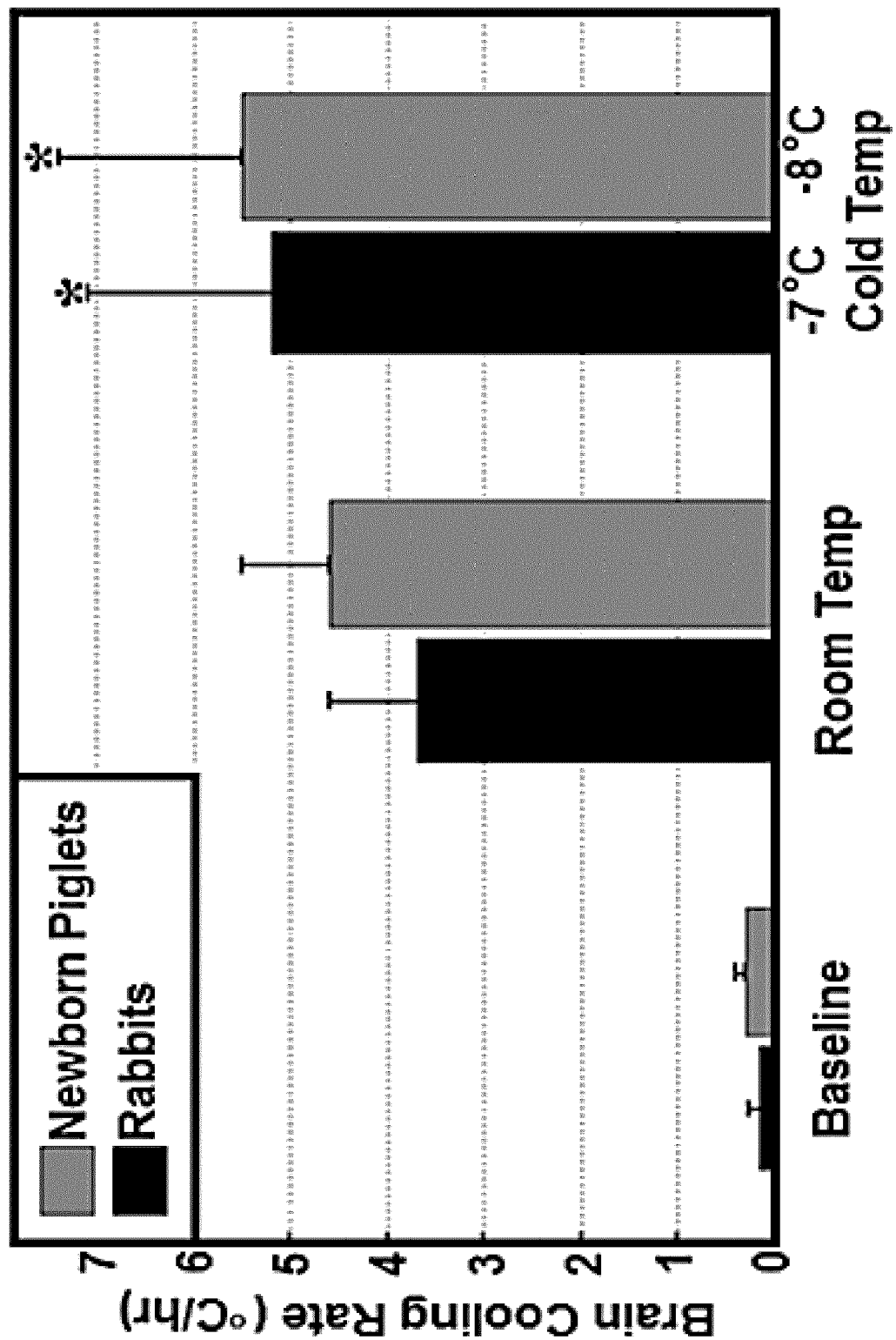
FIG. 12 shows mean data from the sixth experimental test—mean brain cooling rate with different nasopharyngeal cooling methods on rabbits and newborn piglets. * signifies a statistically significant (P<0.05) difference between cold temp versus room temp.

FIG. 12 shows the average brain cooling rates achieved using the nasopharyngeal brain cooling method with either room temperature or cold air at a flow rate of 14-15 L/min for rabbits and newborn piglets. Brain cooling rate was significantly greater with cold than room temperature air in both species. The brain cooling rates achieved in rabbits versus newborn piglets using the nasopharyngeal cooling method with either cold or room temperature air were not significantly different.

Figure 10:
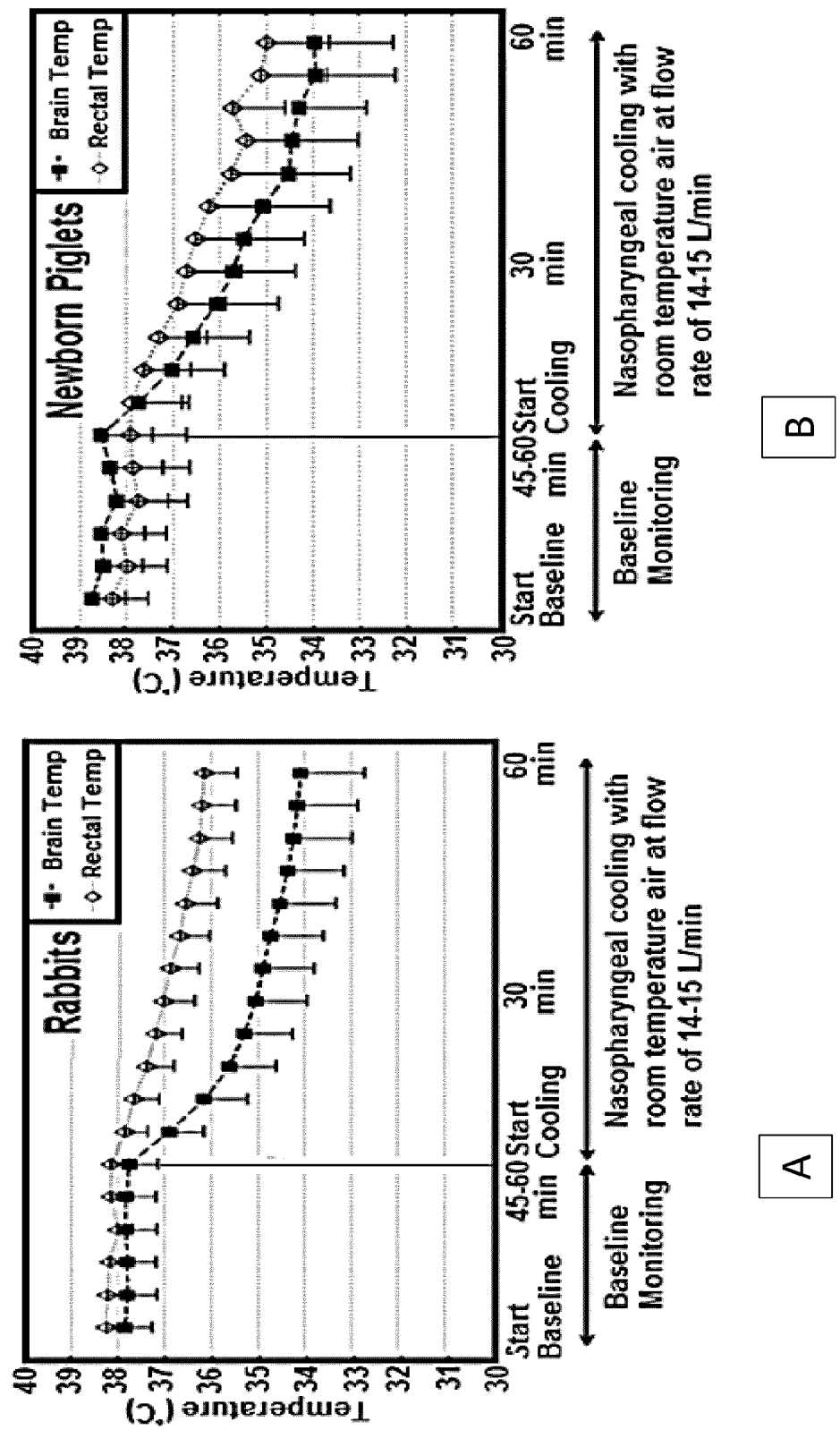
FIG. 10 shows data from the sixth experimental test—brain and rectal temperature over time for nasopharyngeal cooling method with room temperature air at a flow rate of 14-15 L/min on (a) rabbits (N=6) and (b) newborn piglets (N=6)
Figure 11:
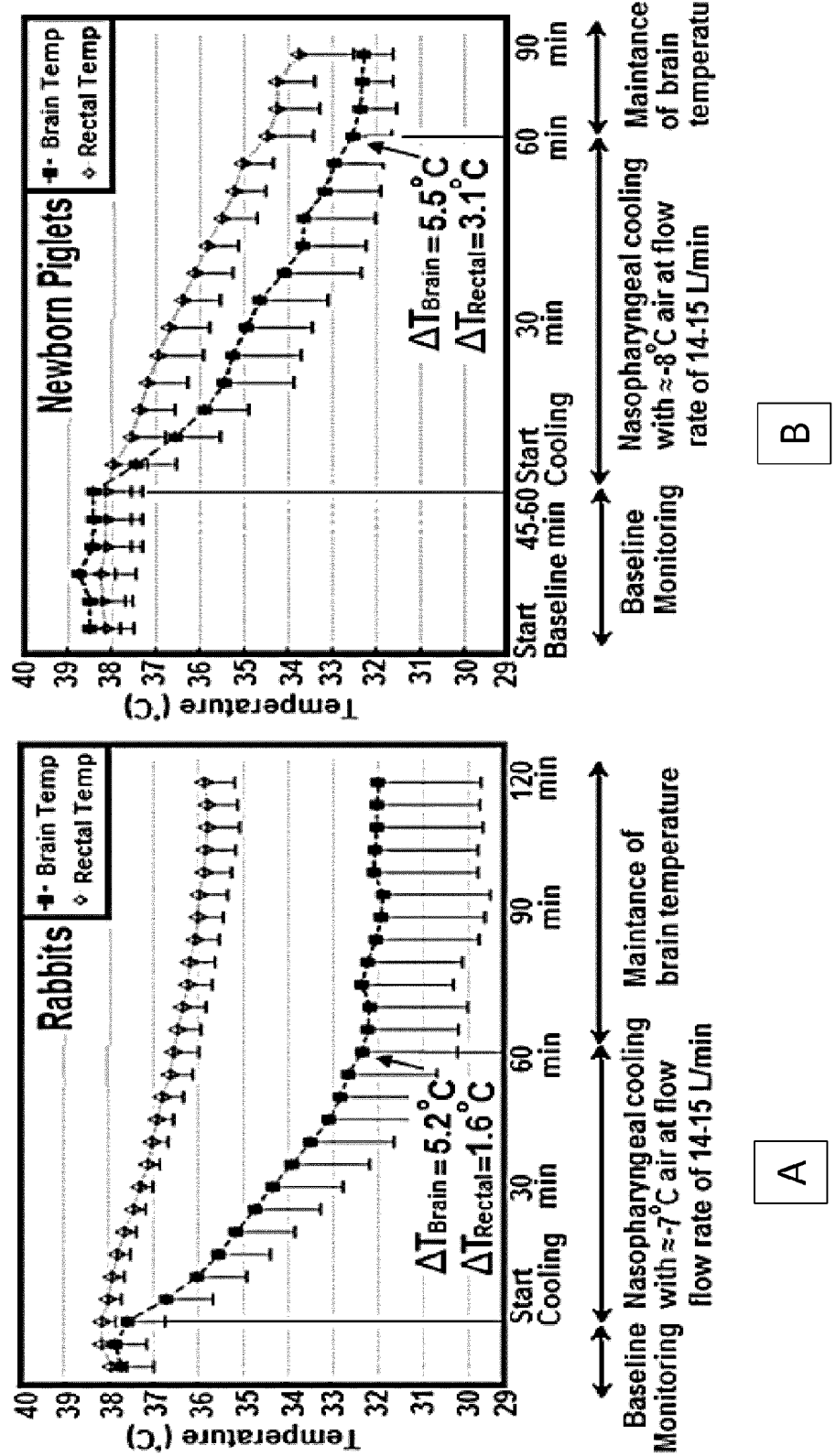
FIG. 11 shows data from the sixth experimental test—brain and rectal temperature over time for nasopharyngeal cooling method with cold air ≈−7° C.) at a flow rate of 14-15 L/min on (a) rabbits (N=6) and (b) newborn piglets (N=6)

FIGS. 10, 11 and 12 show that blowing cooled air produced by the vortex tube into nasal cavities is an effective method to selectively reduce and maintain brain temperature in mammals without carotid rete (rabbits) as well as those with carotid rete (piglets). In both animal species, nasopharyngeal brain cooling was accomplished with the same technique by blowing room temperature or cold air temperature (−8±2° C.) into the nostrils at a flow rate of 14-15 L/min. The only difference is in the source of cold (−7° or −8° C.) air; for the rabbit experiments, the cold (−7° C.) air was produced with a vortex tube whereas for the piglet experiments, cold air (−8° C.) was from an in-house heat exchanger.

The sixth experimental test again demonstrates that the head cooling system comprising the vortex tube allows initial rapid and selective brain cooling. In addition, it maintains a significant gradient between the core and brain temperatures throughout the entire hypothermic period, maximizing the neuroprotective effects while minimizing possible systemic complications. However, the only disadvantage experienced with the use of the vortex tube during experiments was the continuous noise of escaping air, which can be minimized by conventional techniques such as installing all components in a mobile enclosed cart, which is commercially available. No device-related adverse events were observed. No incidences of catheter thrombosis, acute infection, or other complications associated with the insertion procedure were observed.

The head cooling system provides a basis for useful medical intervention, for example, to ameliorate brain damage from hypoxia-ischemia in newborns, traumatic brain injuries in children and adults, resuscitated cardiac arrest patients and in stroke patients. Furthermore, it should be outlined that the cooling system is inexpensive and reusable which may also be an important argument for a wide spread use of this system. The nasopharyngeal air cooling method can be easily implemented in hospitals and even on ambulances by emergency medical services (EMS) personnel in the field; to create a simple "bridge" to other cooling methods used after hospital admission to selectively cool down the brain.

An illustrative version and several variants of a head cooling system and method have been described above without any intended loss of generality. Further variants, modifications and combinations thereof are contemplated and will be apparent to the person of skill in the art.

For example, the head cooling system may be configured to prophylactically or therapeutically treat any neurodegenerative condition including neurodegeneration from neurodegenerative disease, neurodegeneration from ischemic or anoxic events for example stroke, cardiac arrest, respiratory arrest, birth asphyxia, suffocation, drowning, strangulation, electrocution or neurodegeneration from any head or body trauma that disrupts the flow of oxygenated blood to the brain. A few illustrative examples of neurodegenerative disease include Alzheimer's, Parkinson's, Amyotrophic lateral sclerosis, Huntington's, diseases characterized by cognitive impairment and the like.

The head cooling system may accommodate many variations of nasal cannula or face mask including pediatric, adult, or geriatric types. Considerations for size and fit of face masks are well recognized. Considerations for size and fit of nasal cannula are also well recognized. Nasal prong length will generally be greater than about 0.5 cm. Typically, for a subject of pubescent age or older, to better direct cooled gas to the subject's nasopharyngeal cavity the nasal prong length will be greater than about 1 cm. A nasal prong length of greater than about 2 cm may provide a further benefit for directing cooled gas to a nasopharyngeal cavity. The skilled person with routine testing can determine an appropriate nasal prong length for a particular application such as pediatric, pubescent, adult, geriatric, trauma, neurodegenerative disorder, sleep apnea, and the like. In certain examples, the nasal prong length is greater than 1 cm, 2 cm, 3 cm, 4 cm, 5 cm, 6 cm or greater than any length therebetween.

Many types of interface devices are contemplated. For example, face masks including CPAP face masks, nasal cannula, nasal/oral cannula, face masks incorporating nasal cannula, face mask or cannula in combination with an outlet for blowing cooled gas on a surface of a head, and the like may be applicable in the head cooling system. Moreover, a hose connecting to the cold gas outlet of the vortex tube maybe a single hose or may be split from a single connection with the cold gas outlet to two, three or four hoses to direct cooled gas to different surfaces or locations. Bifurcated hoses with V-shaped and Y-shaped configurations are commercially available. In an example with a bifurcated hose, a hose outlet of a first arm of the hose can be connected to an interface such as a face mask or cannula, while a hose outlet of a second arm of the hose may remain unconnected to allow cooled gas to be directed to a surface of a subject's head or neck for surface cooling.

The head cooling system may accommodate any vortex tube that comprises a gas inlet that can be operably connected to the source of compressed breathable gas, a hot gas outlet and a cold gas outlet that can be operably connected to an interface for delivering cooled gas to a nasopharyngeal cavity of a subject. The working of the vortex tube for selective brain cooling can be characterized by two parameters: the inlet air pressure in psig and the flow rate at the cold gas outlet. For example, an illustrative working range of the inlet air pressure can be between about 25 and about 75 psig and an illustrative working range of the flow rate at the cold gas outlet can be between about 15 to about 75 L/min. Vortex tubes may be adapted as needed for specific applications of the head cooling system. For example, a vortex tube comprising a hot gas outlet and a cold gas outlet each with its muffler to reduce noise may be used. As another example, a vortex tube with a bladder connected to the hot gas outlet, such as an annular bladder that extends from the hot gas outlet may be used to warm the core body of a subject to further localize the cooling effect of the head cooling system to the skull, and more particularly the brain region. As yet another example, an automated control unit to regulate the flow rate and/or temperature to desired levels at the cold gas outlet of the vortex tube may be used.

Figure 13:
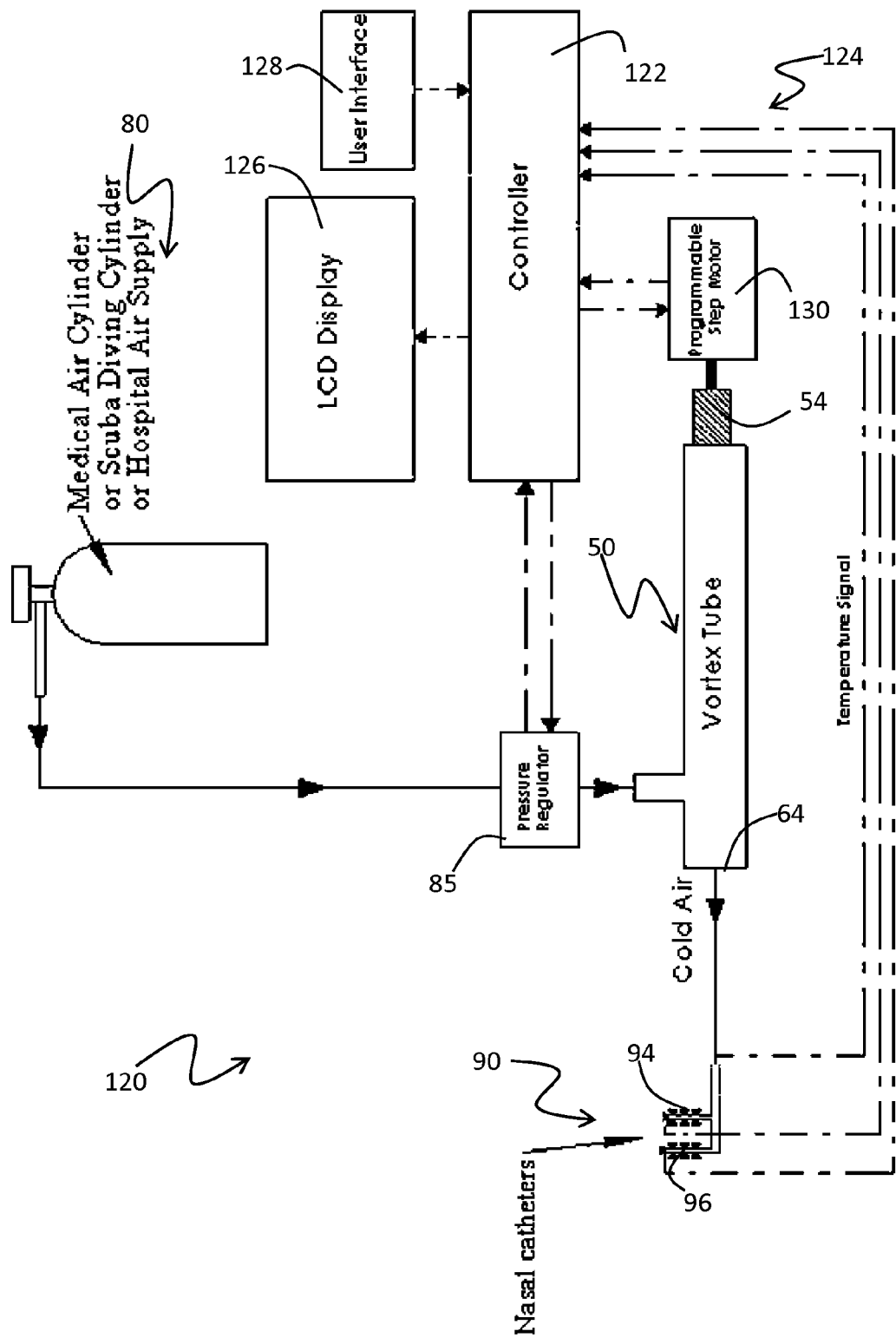
FIG. 13 shows a detailed schematic of a computer-automated variant of the head cooling system shown in FIG. 3.
Figure 14:
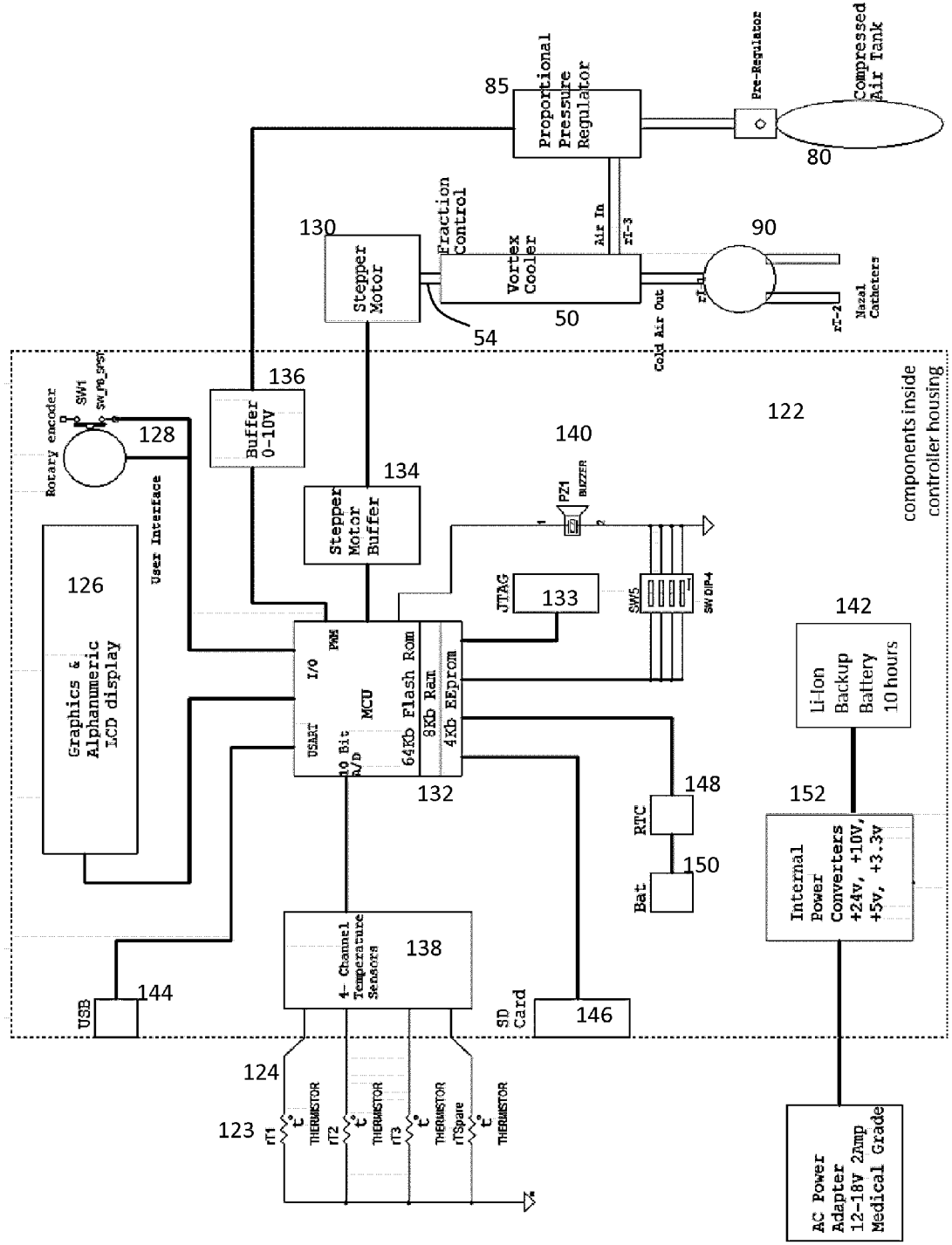
FIG. 14 shows a further detailed block schematic of the computer-automated variant of the head cooling system shown in FIG. 13.

The head cooling system may accommodate various forms of computer-implemented regulation. An example of a variant head cooling system 120 including an automated control unit 122 is shown in FIGS. 13 and 14. The operation of the vortex tube 50 is monitored and regulated by a microprocessor 132 based digital controller 122 that includes feedback connections 124 to automatically control both temperature and gas flow rate at the cold gas outlet 64 of the vortex tube 50. Both input compressed gas pressure flowing through an electrically controllable pressure regulator 85 and fraction control valve 54 settings are adjusted automatically according to an internal look-up table based on the desired temperature and gas flow rate at the cold gas outlet of the vortex tube 50. The internal look-up table may be stored in a memory device operably connected or incorporated within microprocessor 132. Microprocessor 132 may comprise one or more of program flash memory, Random Access Memory, Electrically Erasable Memory, Analog to Digital Converter, Master Clock, multiple Input/Output lines, JTAG interface, USARTs, PWM plus other logic components. A Joint Test Action Group (JTAG) component 133 can provide a diagnostic and programming interface to the microprocessor.

Adjustment of the fraction control valve 54 may be automated using any convenient mechanism including, for example, a programmable stepper motor 130. A stepper motor buffer 134 operably connected between the microprocessor 132 and the programmable stepper motor 130 provides increased drive current for stepper motor control signals. Pressure regulator 85 may be any electrically controllable pressure regulator such as an electro pneumatic pressure regulator, and adjustment of pressure regulator 85 may be automated using an convenient mechanism including, for example, control signals communicated from microprocessor 132. A voltage buffer 136 may be operably connected between microprocessor 132 and pressure regulator 85 to provide a control voltage to the pressure regulator.

Thermistors 123 located at the cold gas outlet 64 and/or at the tips of each of the nasal prongs 94 and 96 of the nasal catheter 90 provide temperature feedback and fault monitoring. Thermistors 123 or temperature sensors are connected to a multiple channel temperature sensor input interface 138 that is operably connected to microprocessor 132. The microprocessor is configured to receive a temperature signal from the temperature sensor 123 and to determine the temperature level of the breathable gas flowing through the interface device and regulate a pressure of the breathable gas if the temperature level is outside a desired or predetermined temperature level range. The predetermined temperature range will typically be bound by first and second limits that are both colder than room temperature. In certain examples, at least one limit of the predetermined temperature level range is approximately 10° C., 9° C., 8° C., 7° C., 6° C., 5° C., 4° C., 3° C., 2° C., 1° C., 0° C., −1° C., −2° C., −3° C., −4° C., −5° C., −6° C., −7° C., −8° C., −9° C., −10° C., −11° C., −12° C., −13° C., −14° C., −15° C., −16° C., −17° C., −18° C., −19° C., or −20° C. In another example, the microprocessor may generate a control signal to regulate pressure if a temperature level is warmer than a threshold temperature. For example, the microprocessor may control a pressure regulator to change from a first pressure setting to a second pressure setting if the temperature level is greater than a desired or predetermined threshold temperature. The threshold temperature may be any temperature less than room temperature. Typically, the threshold temperature is less than 10° C. In certain examples, the threshold temperature is approximately 10° C., 9° C., 8° C., 7° C., 6° C., 5° C., 4° C., 3° C., 2° C., 1° C., 0° C., −1° C., −2° C., −3° C., −4° C., −5° C., −6° C., −7° C., −8° C., −9° C., −10° C., −11° C., −12° C., −13° C., −14° C., or −15° C. The desired temperature and flow rate may be entered by the operator or selected from pre-defined protocols using an LCD display screen 126 and operator input device 128. The display screen 126 may provide information in graphical and/or alphanumerical formats. The operator input device 128 may comprise a rotary encoder with an integral push button allowing a user to make on-screen selections and various control points. The operator input device may also comprise a multiple position selection switch allowing a user to select pre-set functions.

The internal look-up table is pre-calibrated to provide an initial starting point for both input compressed gas pressure and cold fraction output for the vortex tube to achieve the desired temperature and flow rate at the cold gas outlet 64. The automated control unit can continuously monitor run time and temperatures to alert the operator if there is a problem or when the supply gas reservoir (tank) 80 is running out. This may be done by audio alarm 140 and/or by on screen alerts. The control system may include an internal rechargeable battery 142 so it can operate for extended periods without external power. This can be useful for application of the cooling system in areas where there is no access to electrical power. The controller 122 will typically include one or more internal power converters 152 to provide current to internal power supplies including a battery charger.

Data log files can be available for personal computer download via a Universal Serial Bus (USB) port 144. The USB port may permit communication with many different types of external devices. Program updates or protocol files can be loaded from a Secure Data (SD) card connector 146. The SD card interface/slot may also provide for remote storage of data. The controller 122 may comprise a real time clock 148 with battery backup 150 to supply time and date to microprocessor 130.

The computer-implemented regulation of the head cooling system typically requires a memory, an interface and a processor. The types and arrangements of memory, interface and processor may be varied according to implementations. For example, the interface may include a software interface that communicates with an end-user computing device through an Internet connection. The interface may also include a physical electronic device configured to receive requests or queries from an end-user.

Although a microprocessor is described with reference to FIGS. 13 and 14, many other computer device types may be used including for example, a programmable logic controller or a field programmable logic array. Moreover, any conventional computer architecture may be used for computer-implemented regulation of the head cooling system including for example a memory, a mass storage device, a processor (CPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the head cooling system for nasopharyngeal cooling can be stored within memory and then retrieved and processed via processor to perform a particular task or function. Similarly, one or more nasopharyngeal cooling protocols may be encoded as a program component, stored as executable instructions within memory and then retrieved and processed via a processor. A user input device, such as a keyboard, mouse, or another pointing device, can be connected to PCI (Peripheral Component Interconnect) bus. The software will typically provide an environment that represents programs, files, options, and so forth by means of graphically displayed icons, menus, and dialog boxes on a computer monitor screen.

A data-process apparatus can include CPU, ROM, and RAM, which are also coupled to a PCI (Peripheral Component Interconnect) local bus of data-processing apparatus through PCI Host Bridge. The PCI Host Bridge can provide a low latency path through which processor may directly access PCI devices mapped anywhere within bus memory and/or input/output (I/O) address spaces. PCI Host Bridge can also provide a high bandwidth path for allowing PCI devices to directly access RAM.

A communications adapter, a small computer system interface (SCSI), and an expansion bus-bridge may also be attached to PCI local bus. The communications adapter can be utilized for connecting data-processing apparatus to a network. SCSI can be utilized to control a high-speed SCSI disk drive. An expansion bus-bridge, such as a PCI-to-ISA bus bridge, may be utilized for coupling ISA bus to PCI local bus. PCI local bus can be connected to a monitor, which functions as a display (e.g., a video monitor) for displaying data and information for an operator and also for interactively displaying a graphical user interface.

Computer-implemented regulation of the head cooling system may accommodate any type of end-user computing device including computing devices communicating over a networked connection. The computing device may display graphical interface elements for performing the various functions of the system such as selecting a pre-set nasopharyngeal cooling protocol, modifying an existing nasopharyngeal cooling protocol, or updating a database of an activity log that may be locally stored in the computing device. For example, the computing device may be a desktop, laptop, notebook, tablet, personal digital assistant (PDA), PDA phone or smartphone, gaming console, portable media player, and the like. The computing device may be implemented using any appropriate combination of hardware and/or software configured for wired and/or wireless communication. Communication can occur over a network, for example, where remote control of the head cooling system is desired.

If a networked connection is desired the head cooling system may accommodate any type of network. The network may be a single network or a combination of multiple networks. For example, the network may include the internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

The computer-automated head cooling system described herein and each variant, modification or combination thereof may also be implemented as a method or code on a computer readable medium (i.e. a substrate). The computer readable medium is a tangible data storage device that can store data, which can thereafter, be read by a computer system. Examples of a computer readable medium include read-only memory, random-access memory, CD-ROMs, magnetic tape, SD card, optical data storage devices and the like. The computer readable medium may be geographically localized or may be distributed over a network coupled computer system so that the computer readable code is stored and executed in a distributed fashion.

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. A head cooling system comprising:
   a source of compressed breathable gas;
   a vortex tube comprising an inlet, a hot gas outlet and a cold gas outlet, the inlet operably connected to the source of compressed breathable gas;
   a nasal cannula configured to deliver cooled gas to the nasopharyngeal cavity of a subject, in fluid communication with the cold gas outlet; and
   a bladder in fluid communication with the hot gas outlet, the bladder capturing at least a portion of gas flowing from the hot gas outlet, and the bladder sized and shaped to provide an exterior surface to contact a body region located between a neck and a pelvis of the subject.

2. The system of claim 1, further comprising a temperature sensor coupled at or proximal to the nasal cannula, the temperature sensor generating a temperature signal indicative of a temperature level of the breathable gas flowing through the nasal cannula.

3. The system of claim 2, further comprising a computer operably connected to the temperature sensor, the computer configured to receive the temperature signal and to determine the temperature level of the breathable gas and regulate a pressure of the breathable gas if the temperature level is outside of a predetermined temperature range.

4. The system of claim 3, further comprising a pressure regulator fluidly coupled between the source of compressed breathable gas and the inlet of the vortex tube, the computer configured to generate a control signal to induce the pressure regulator to change from a first pressure setting to a second pressure setting if the temperature level is outside of the predetermined temperature range.

5. The system of claim 1, wherein the vortex tube comprises an adjustable fraction control valve for adjusting the flow of hot gas at the hot gas outlet.

6. The system of claim 5, further comprising a computer operably connected to the fraction control valve, the computer configured to generate a control signal to induce the fraction control valve to change from a first setting to a second setting when the computer determines that a temperature level of breathable gas flowing through the nasal cannula is outside of a predetermined temperature range.

7. The system of claim 1, wherein the vortex tube comprises a muffler in fluid communication with the hot air outlet, a muffler in fluid communication with the cold air outlet, or a muffler in fluid communication with each of the hot air outlet and the cold air outlet respectively.

8. The system of claim 1, wherein the nasal cannula is a Continuous Positive Air Pressure (CPAP) nasal cannula for treatment of sleep apnea.

9. The system of claim 1, wherein the nasal cannula comprises two substantially parallel nasal prongs for insertion into nostrils, and each nasal prong is at least 2 centimeters in length and comprises at least one aperture for outlet of cooled gas.

10. The system of claim 1, wherein the bladder has an annular shape.

11. The system of claim 1, further comprising an oral cannula in fluid communication with the cold gas outlet.

12. A head cooling kit comprising:
a vortex tube comprising an inlet, a hot gas outlet and a cold gas outlet;
a nasal cannula configured to deliver cooled gas to the nasopharyngeal cavity, in fluid communication with the cold gas outlet;
instructions for operably connecting the inlet to a source of compressed breathable gas and securing the nasal cannula to a mammal; and
a bladder in fluid communication with the hot gas outlet, the bladder capturing at least a portion of gas flowing from the hot gas outlet, and the bladder sized and shaped to provide an exterior surface to contact a body region located between a neck and a pelvis.

13. The kit of claim 12, further comprising a temperature sensor coupled at or proximal to the nasal cannula, the temperature sensor generating a temperature signal indicative of a temperature level of the breathable gas flowing through the nasal cannula.

14. The kit of claim 13, further comprising a computer operably connected to the temperature sensor, the computer configured to receive the temperature signal and to determine the temperature level of the breathable gas and regulate a pressure of the breathable gas if the temperature level is outside of a predetermined temperature range.

15. The kit of claim 14, further comprising a pressure regulator fluidly coupled between the source of compressed breathable gas and the inlet of the vortex tube, the computer configured to generate a control signal to induce the pressure regulator to change from a first pressure setting to a second pressure setting if the temperature level is outside of the predetermined temperature range.

16. The kit of claim 12, wherein the vortex tube comprises an adjustable fraction control valve for adjusting the flow of hot gas at the hot gas outlet.

17. The kit of claim 16, further comprising a computer operably connected to the fraction control valve, the computer configured to generate a control signal to induce the fraction control valve to change from a first setting to a second setting when the computer determines that a temperature level of breathable gas flowing through the nasal cannula is outside of a predetermined temperature range.

18. The kit of claim 12, wherein the vortex tube comprises a muffler in fluid communication with the hot air outlet, a muffler in fluid communication with the cold air outlet, or a muffler in fluid communication with each of the hot air outlet and the cold air outlet respectively.

19. The kit of claim 12, wherein the nasal cannula is a Continuous Positive Air Pressure (CPAP) nasal cannula for treatment of sleep apnea.

20. The kit of claim 12, wherein the nasal cannula comprises two substantially parallel nasal prongs for insertion into nostrils, and each nasal prong is at least 2 centimeters in length and comprises at least one aperture for outlet of cooled gas.

21. The kit of claim 12, wherein the bladder has an annular shape.

22. The kit of claim 12, further comprising an oral cannula in fluid communication with the cold gas outlet.

* * * * *